United States Patent
Cockerill et al.

(10) Patent No.: US 10,106,539 B2
(45) Date of Patent: Oct. 23, 2018

(54) SPIRO-INDOLINES FOR THE TREATMENT AND PROPHYLAXIS OF RESPIRATORY SYNCYTIAL VIRUS INFECTION (RSV)

(71) Applicant: REVIRAL LIMITED, Stevenage (GB)

(72) Inventors: Stuart Cockerill, Stevenage (GB); Neil Mathews, Stevenage (GB); Simon Ward, Sussex (GB); Graham Lunn, Sussex (GB); Michael Paradowski, Sussex (GB); Jose Miguel Gascon Simorte, Sussex (GB)

(73) Assignee: REVIRAL LIMITED, Stevenage (GB)

( * ) Notice: Subject to any disclaimer, the term of this patent is extended or adjusted under 35 U.S.C. 154(b) by 0 days.

(21) Appl. No.: 15/517,290

(22) PCT Filed: Oct. 6, 2015

(86) PCT No.: PCT/GB2015/052920
§ 371 (c)(1),
(2) Date: Apr. 6, 2017

(87) PCT Pub. No.: WO2016/055780
PCT Pub. Date: Apr. 14, 2016

(65) Prior Publication Data
US 2017/0305908 A1    Oct. 26, 2017

(30) Foreign Application Priority Data
Oct. 7, 2014   (GB) .................................. 1417707.5

(51) Int. Cl.
| | | |
|---|---|---|
| *C07D 471/10* | (2006.01) | |
| *C07D 403/06* | (2006.01) | |
| *C07D 401/06* | (2006.01) | |
| *A61K 31/416* | (2006.01) | |
| *A61K 31/4184* | (2006.01) | |
| *A61K 31/437* | (2006.01) | |
| *C07D 405/14* | (2006.01) | |

(52) U.S. Cl.
CPC .......... *C07D 471/10* (2013.01); *A61K 31/416* (2013.01); *A61K 31/4184* (2013.01); *A61K 31/437* (2013.01); *C07D 401/06* (2013.01); *C07D 403/06* (2013.01); *C07D 405/14* (2013.01)

(58) Field of Classification Search
CPC ............................. C07D 471/10; C07D 403/06
See application file for complete search history.

(56) References Cited

U.S. PATENT DOCUMENTS

| 9,809,575 B2 * | 11/2017 | Cockerill | .............. | C07D 403/06 |
| 2010/0278835 A1 | 11/2010 | Blade et al. | | |
| 2014/0308282 A1 * | 10/2014 | Cockerill | .............. | C07D 401/06 424/134.1 |

FOREIGN PATENT DOCUMENTS

| WO | WO 02/062290 A2 | 8/2002 |
| WO | WO 03/053344 A2 | 7/2003 |
| WO | WO 2004/092168 A1 | 10/2004 |
| WO | WO 2006/031606 A2 | 3/2006 |
| WO | WO 2006/044504 A1 | 4/2006 |
| WO | WO 2010/103306 A1 | 9/2010 |
| WO | WO-2013/068769 A1 * | 5/2013 |
| WO | WO 2013/068769 A1 | 5/2013 |
| WO | WO 2014/060411 A1 | 4/2014 |
| WO | WO-2014/184163 A1 * | 11/2014 |
| WO | WO 2014/184163 A1 | 11/2014 |
| WO | WO-2015/022263 A1 * | 2/2015 |
| WO | WO 2015/022263 A1 | 2/2015 |
| WO | WO 2015/022301 A1 | 2/2015 |

OTHER PUBLICATIONS

Chemical Abstracts Registry No. 1659186-28-3, indexed in the Registry file on STN CAS Online Mar. 10, 2015.*
Chemical Abstracts Registry No. 1659186-13-6, indexed in the Registry file on STN CAS Online Mar. 10, 2015.*
Chemical Abstracts Registry No. 1659186-33-0, indexed in the Registry file on STN CAS Online Mar. 10, 2015.*
European Patent Office, International Search Report and Written Opinion issued in International Application No. PCT/GB2016/052920 (dated Dec. 7, 2015).
International Bureau of WIPO, International Preliminary Report on Patentability issued in International Application No. PCT/GB2016/052920 (dated Apr. 20, 2017).
Cianci et al., "Oral Efficacy of a Respiratory Syncytial Virus Inhibitor in Rodent Models of Infection", *Antimicrobial Agents and Chemotherapy*, 48(7): 2448-2454 (2004).

(Continued)

*Primary Examiner* — Laura L Stockton
(74) *Attorney, Agent, or Firm* — Leydig, Voit & Mayer, Ltd.

(57) ABSTRACT

Benzimidazoles of formula (I): wherein: one of X and Y is an N atom or a substituted C atom, and the other is CH; L is a single bond, $C_{1-3}$ alkylene, $C_{2-3}$ alkenylene or $C_{2-3}$ alkynylene; $R^1$ is $C_{1-6}$ alkyl, $C_{2-6}$ alkenyl, $C_{2-6}$ alkynyl, 3- to 10-membered cycloalkyl, 5- to 10-membered heterocyclyl or 5- to 12-membered heteroaryl, each of which is unsubstituted or substituted; Z is halo, $C_{1-6}$ haloalkyl, nitro, —CN, —N($R^2$)$_2$, —O$R^2$, —S$R^2$, —S(=O)$R^2$, or —S(=O)$_2R^2$; each $R^2$ is independently hydrogen, $C_{1-6}$ alkyl, $C_{2-6}$ alkenyl or C2-6 alkynyl, wherein said alkyl, alkenyl and alkynyl groups are unsubstituted or substituted; and m is 0 or 1; and the pharmaceutically acceptable salt thereof are inhibitors of RSV and can therefore be used to treat or prevent an RSV infection.

Formula (I)

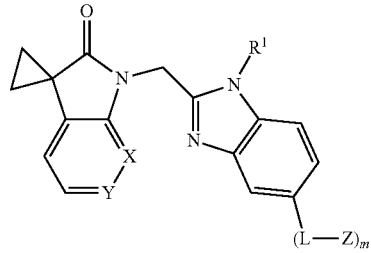

12 Claims, No Drawings

(56) References Cited

OTHER PUBLICATIONS

Combrink et al., "Respiratory syncytial virus fusion inhibitors. Part 6: An examination of the effect of structural variation of the benzimidazol-2-one heterocycle moiety", *Bioorganic & Medicinal Chemistry Letters*, 17: 4784-4790 (2007).
Pryde et al., "Non-benzimidazole containing inhibitors of respiratory syncytial virus", *Bioorganic & Medicinal Chemistry Letters*, 23(3): 827-833 (2013).
Viswanadhan et al., "Atomic Physicochemical Parameters for Three Dimensional Structure Directed Quantitative Structure-Activity Relationships. 4. Additional Parameters for Hydrophobic and Dispersive Interactions and Their Application for an Automated Superposition of Certain Naturally Occurring Nucleoside Antibiotics", *J. Chem. Inf. Comput. Sci.*, 29: 163-172 (1989).

\* cited by examiner

SPIRO-INDOLINES FOR THE TREATMENT AND PROPHYLAXIS OF RESPIRATORY SYNCYTIAL VIRUS INFECTION (RSV)

FIELD OF THE INVENTION

The present invention relates to benzimidazole compounds and to their use in treating or preventing a respiratory syncytial virus (RSV) infection.

BACKGROUND TO THE INVENTION

RSV is a negative-sense, single-stranded RNA virus of the Paramyxoviridae family. RSV is readily transmitted by secretions from an infected person via surfaces or hand-to-hand transfer. Unlike influenza, it is not transmitted by small-particle aerosols. Following successful inoculation, the incubation period is between four and six days during which time the virus spreads from the nasopharynx to the lower respiratory tract by fusion of infected with uninfected cells and by sloughing of the necrotic epithelium. In infants, coupled with increased mucus secretion and oedema, this can lead to mucus plugging causing hyper-inflation and collapse of distal lung tissue indicative of bronchiolitis. Hypoxia is common and the ability to feed is often impaired because of respiratory distress. In RSV pneumonia, inflammatory infiltration of the airways consists of mononuclear cells and is more generalised, with involvement of the bronchioles, bronchi and alveoli. The duration and degree of viral shedding has been found to correlate with the clinical signs and severity of disease.

RSV is the leading cause of serious respiratory tract infections in infants and young children throughout the world. The highest morbidity and mortality occurs in those born prematurely and for those with chronic lung or heart disease, although many infants hospitalised for RSV infection are otherwise healthy. Severe RSV infection in infancy can lead to several years of recurrent wheezing and is linked to the later development of asthma.

RSV is also a major cause of morbidity and mortality in the elderly and in immunocompromised children and adults as well as those with chronic obstructive pulmonary disease (COPD) and congestive heart failure (CHF).

RSV has a seasonal incidence; it is highly predictable and occurs in the winters of both hemispheres, from September to May in Europe and North America, peaking in December and January, and can occur throughout the year in tropical countries. It affects >90% of infants and young children by the age of two years and as natural immunity is short-lived; many will be re-infected each year. As with influenza, in elderly people, RSV causes around 10% of winter hospitalisations with an associated mortality of 10%.

Current anti-RSV treatment involves the use of a monoclonal antibody to RSV, called palivizumab. Such use of palivizumab is a prophylactic, rather than therapeutic, treatment of RSV. Although this antibody is often effective, its use is restricted to preterm infants and infants at high risk. Indeed, its limited utility means that it is unavailable for many people in need of anti-RSV treatment. There is therefore an urgent need for effective alternatives to existing anti-RSV treatment.

Additionally, several compounds have been proposed as inhibitors of RSV, including benzimidazole-based compounds. For example, K D Combrink et al., Bioorganic & Medicinal Chemistry Letters, 17 (2007), 4784-4790 discloses the compound BMS-433771 and variants thereof. Further benzimidazole-based compounds are disclosed in WO-02/062290, WO-03/053344 and WO-10/103306.

WO 2013/068769 discloses spirocyclic compounds having activity against RSV. However there exists a need to identify further compounds, and in particular compounds having favourable pharmacokinetic profiles.

SUMMARY OF THE INVENTION

It has now been found that a novel series of benzimidazoles are active as RSV inhibitors with favourable pharmacokinetics.

Accordingly, the present invention provides a compound which is a benzimidazole of formula (I):

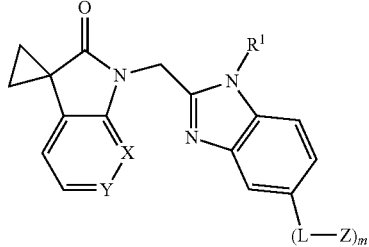

Formula (I)

wherein:
one of X and Y is an N atom or a substituted C atom, and the other is CH;
L is a single bond, $C_{1-3}$ alkylene, $C_{2-3}$ alkenylene or $C_{2-3}$ alkynylene;
$R^1$ is $C_{1-6}$ alkyl, $C_{2-6}$ alkenyl, $C_{2-6}$ alkynyl, 3- to 10-membered cycloalkyl 5- to 10-membered heterocyclyl or 5- to 12-membered heteroaryl, each of which is unsubstituted or substituted;
Z is halo, $C_{1-6}$ haloalkyl, nitro, —CN, —N$(R^2)_2$, —OR$^2$, —SR$^2$, —S(=O)R$^2$, or —S(=O)$_2$R$^2$;
each $R^2$ is independently hydrogen, $C_{1-6}$ alkyl, $C_{2-6}$ alkenyl or $C_{2-6}$ alkynyl, wherein said alkyl, alkenyl and alkynyl groups are unsubstituted or substituted; and
m is 0 or 1;
or a pharmaceutically acceptable salt thereof.

DETAILED DESCRIPTION OF THE INVENTION

When any group, ring, substituent or moiety defined herein is substituted, it is typically substituted by Q as defined below.

A $C_{1-6}$ alkyl group or moiety is linear or branched. A $C_{1-6}$ alkyl group is typically a $C_{1-4}$ alkyl group, or a $C_{4-6}$ alkyl group. Examples of $C_{1-6}$ alkyl groups and moieties include methyl, ethyl, n-propyl, i-propyl, n-butyl, i-butyl, t-butyl, n-pentyl, i-pentyl (i.e. 3-methylbut-1-yl), t-pentyl (i.e. 2-methylbut-2-yl), neopentyl (i.e. 2,2-dimethylpropan-1-yl), n-hexyl, i-hexyl (i.e. 4-methylpentan-1-yl), t-hexyl (i.e. 3-methylpentan-3-yl) and neopentyl (i.e. 3,3-dimethylbutan-1-yl). For the avoidance of doubt, where two alkyl moieties are present in a group, the alkyl moieties may be the same or different. A $C_{1-6}$ alkyl group is unsubstituted or substituted, typically by one or more groups Q as defined below. For example, a $C_{1-6}$ alkyl group is unsubstituted or substituted by 1, 2 or 3 groups Q as defined below.

Q is halo, nitro, —CN, OH, $C_{1-6}$ alkoxy, $C_{1-6}$ hydroxyalkyl, $C_{1-6}$ alkylthio, $C_{1-6}$ haloalkyl, $C_{1-4}$ haloalkoxy, —CO$_2$R'''$_2$, —NR'''$_2$, —SR''', —S(=O)R''', —S(=O)$_2$R''', $C_3$-$C_{10}$ cycloalkyl, 5 to 10-membered heterocyclyl, 5- to 12-membered aryl or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

A $C_{1-3}$ alkylene group or moiety is an unsubstituted or substituted, linear or branched, saturated divalent aliphatic hydrocarbon group or moiety containing 1 to 3 carbon atoms. Examples include methylene, ethylene, n-propylene and i-propylene groups and moieties. When the alkylene group is substituted it is typically substituted by a group Q as defined above.

A $C_{2-6}$ alkenyl group is an unsubstituted or substituted, linear or branched hydrocarbon radical of two to six carbon atoms with at least one site of unsaturation, i.e., a carbon-carbon sp$^2$ double bond. An alkenyl group may have "cis" or "trans" orientation, or alternatively "E" or "Z" orientation. Typically it is a $C_{2-4}$ alkenyl group or a $C_{4-6}$ alkenyl group. Examples include ethylenyl or vinyl (—CH=CH$_2$), and allyl (—CH$_2$CH=CH$_2$). When the alkenyl group is substituted it is typically substituted by a group Q as defined above.

A $C_{2-3}$ alkenylene group or moiety is linear or branched, unsaturated divalent aliphatic hydrocarbon group or moiety containing two or three carbon atoms with at least one carbon-carbon sp$^2$ double bond. An alkenylene group may have "cis" or "trans" orientation, or alternatively "E" or "Z" orientation. Examples include —CH=CH—, —CH=CHCH$_2$— and —CH$_2$CH=CH— groups and moieties.

A $C_{2-6}$ alkynyl group is an unsubstituted or substituted, linear or branched hydrocarbon radical of two to six carbon atoms with at least one site of unsaturation, i.e., a carbon-carbon sp triple bond. Typically it is a $C_{2-4}$ alkynyl group or a $C_{4-6}$ alkynyl group. An alkynyl group may have "cis" or "trans" orientation, or alternatively "E" or "Z" orientation. Examples include ethynyl (—C≡CH) or propynyl (propargyl, —CH$_2$C≡CH). When an alkynyl group is substituted it is typically substituted by one or more groups Q as defined above A $C_{2-3}$ alkynylene group is a linear, unsaturated divalent aliphatic hydrocarbon group or moiety containing two or three carbon atoms with one carbon-carbon sp triple bond. An alkynylene group may have "cis" or "trans" orientation, or alternatively "E" or "Z" orientation. Examples include —C≡C—, —C≡CCH$_2$— and —CH$_2$C≡C— groups and moieties.

A $C_{1-6}$ alkoxy group is linear or branched. It is typically a $C_{1-4}$ alkoxy group, for example a methoxy, ethoxy, propoxy, i-propoxy, n-propoxy, n-butoxy, sec-butoxy or tert-butoxy group. A $C_{1-6}$ alkoxy group is unsubstituted or substituted, typically by one or more groups Q as defined.

A $C_{1-6}$ alkylthio group is linear or branched. It is typically a $C_{1-4}$ alkylthio group, for example a methylthio, ethylthio, propylthio, i-propylthio, n-propylthio, n-butylthio, sec-butylthio or tert-butylthio group. A $C_{1-6}$ alkylthio group is unsubstituted or substituted, typically by one or more groups Q as defined.

A halogen or halo group is F, Cl, Br or I. Preferably it is F, Cl or Br. A $C_{1-6}$ alkyl group substituted by halogen may be denoted "$C_{1-6}$ haloalkyl", which means a $C_{1-6}$ alkyl group as defined above in which one or more hydrogens is replaced by halo. Likewise a $C_{1-6}$ alkoxy group substituted by halogen may be denoted "$C_{1-6}$ haloalkoxy", which means a $C_{1-6}$ alkoxy group as defined above in which one or more hydrogens is replaced by halo. Typically, $C_{1-6}$ haloalkyl or $C_{1-6}$ haloalkoxy is substituted by 1, 2 or 3 said halogen atoms. Haloalkyl and haloalkoxy groups include perhaloalkyl and perhaloalkoxy groups such as —CX$_3$ and —OCX$_3$ wherein X is a halogen, for example —CF$_3$ —CCl$_3$ —OCF$_3$ and —OCCl$_3$.

A $C_{1-6}$ hydroxyalkyl group is a $C_{1-6}$ alkyl group as defined above, substituted by one or more OH groups. Typically, it is substituted by one, two or three OH groups. Preferably, it is substituted by a single OH group.

A 5- to 12-membered aryl group is an aromatic carbocyclic group containing from 5 to 12 carbon atoms, for instance from 6 to 10 carbon atoms, such as 6 or 10 carbon atoms. It is monocyclic or a fused bicyclic ring system in which an aromatic ring is fused to another aromatic carbocyclic ring. Examples of a 5- to 12-membered aryl group include phenyl and naphthalenyl. When substituted, an aryl group is typically substituted by $C_{1-4}$ alkyl or a group Q as defined above, for instance by 1, 2 or 3, groups selected from a $C_{1-4}$ alkyl group and a group Q as defined above.

An aralkyl group is an aryl group, as defined above, attached to an alkyl group, as defined above. Examples include benzyl.

A $C_{3-10}$ cycloalkyl group is a saturated hydrocarbon ring having from 3 to 10 carbon atoms. A $C_{3-10}$ cycloalkyl group may be, for instance, $C_3$-$C_7$ cycloalkyl such as cyclopropyl, cyclobutyl, cyclopentyl, cyclohexyl, or cycloheptyl. Typically it is $C_3$-$C_6$ cycloalkyl, for example cyclopropyl, cyclobutyl or cyclopentyl. In one embodiment it is cyclopropyl. A $C_{3-10}$ cycloalkyl group is unsubstituted or substituted, typically by one or more groups Q as defined above.

A 5- to 12-membered heteroaryl group or moiety is a 5- to 12-membered aromatic heterocyclic group which contains 1, 2, 3, or 4 heteroatoms selected from O, N and S. It is monocyclic or bicyclic. Typically it contains one N atom and 0, 1, 2 or 3 additional heteroatoms selected from O, S and N. It may be, for example, a 5- to 7-membered heteroaryl group, for instance a 5- or 6-membered N-containing heteroaryl group. Examples include pyridyl, pyrazinyl, pyrimidinyl, pyridazinyl, furanyl, thienyl, pyrazolidinyl, pyrrolyl, oxadiazolyl, oxazolyl, isoxazolyl, thiazolyl, thiadiazolyl, imidazolyl and pyrazolyl groups. Furanyl, thienyl, pyridyl and pyrimidyl groups are preferred. When substituted, a heteroaryl group is typically substituted by one or more, e.g. 1, 2 or 3, groups selected from $C_{1-4}$ alkyl and a group Q as defined above.

A 5- to 10-membered heterocyclyl moiety is a monocyclic or bicyclic non-aromatic, saturated or unsaturated $C_{5-10}$ carbocyclic ring, in which at least one, for example 1, 2 or 3, carbon atoms in the ring are replaced with an atom or group selected from O, S, SO, SO$_2$, CO and N. Typically, it is a saturated $C_{5-10}$ ring in which 1, 2 or 3 of the carbon atoms in the ring are replaced with an atom or group selected from O, S, SO$_2$, CO and NH. More typically it is a monocyclic ring, preferably a monocyclic $C_5$-$C_6$ ring. Examples include piperidyl, piperidin-2,6-dionyl, piperidin-2-onyl, piperazinyl, morpholinyl, thiomorpholinyl, S,S-dioxothiomorpholinyl, 1,3-dioxolanyl, pyrrolidinyl, imidazol-2-onyl, pyrrolidin-2-onyl, tetrahydrofuranyl and tetrahydropyranyl moieties.

For the avoidance of doubt, although the above definitions of heteroaryl and heterocyclyl groups refer to an "N" atom which can be present in the ring, as will be evident to a skilled chemist the N atom will be protonated (or will carry a substituent as defined above) if it is attached to each of the adjacent ring atoms via a single bond. Such protonated forms are embraced within the present definitions of heteroaryl and heterocyclyl groups.

Typically, when one of X and Y is a substituted C atom, it is a C atom substituted with Q as defined above. More typically, when one of X and Y is a substituted C atom, it is a C atom substituted with halo, nitro, —CN, OH, $C_{1-6}$ alkoxy, $C_{1-6}$ hydroxyalkyl, $C_{1-6}$ alkylthio, $C_{1-6}$ haloalkyl, $C_{1-4}$ haloalkoxy, —$CO_2R'''$, —$NR'''_2$, —$SR'''$, —$S(=O)R'''$, or —$S(=O)_2R'''$, wherein each $R'''$ is independently selected from H and $C_{1-6}$ alkyl.

Preferably, when one of X and Y is a substituted C atom, it is a C atom substituted with halo, nitro, —CN, OH, $C_{1-4}$ alkoxy, $C_{1-4}$ hydroxyalkyl, $C_{1-4}$ alkylthio, $C_{1-4}$ haloalkyl, $C_{1-4}$ haloalkoxy, —$CO_2R'''$, —$NR'''_2$, —$SR'''$, —$S(=O)R'''$, or —$S(=O)_2R'''$, wherein each $R'''$ is independently selected from H and $C_{1-4}$ alkyl. More preferably, when one of X and Y is a substituted C atom, it is a C atom substituted with halo, nitro, —CN, OH. Still more preferably, when one of X and Y is a substituted C atom, it is a C atom substituted with a halo atom. Most preferably, when one of X and Y is a substituted C atom, it is a C atom substituted with a fluorine atom.

Thus, in some embodiments, one of X and Y is an N atom or a C atom substituted with a halogen atom, and the other is CH. Typically, in such embodiments one of X and Y is an N atom or C substituted with a fluorine atom, and the other is CH.

In some embodiments, $R^1$ is $C_{1-6}$ alkyl, $C_{2-6}$ alkenyl, $C_{2-6}$ alkynyl, 5- to 10-membered heterocyclyl or 5- to 12-membered heteroaryl, each of which is unsubstituted or substituted.

Typically, when $R^1$ is a heterocyclyl or heteroaryl group, said heterocyclyl or heteroaryl group contains one, two or three heteroatoms, more typically one or two heteroatoms, and preferably one heteroatom. Typically, said heteroatoms are selected from N, O, and S. More typically heteroatoms are selected from N and O. Preferably, said heteroatoms are O.

Typically, when $R^1$ is substituted, it is substituted with one or more groups (e.g. 1, 2, 3 or 4 groups) Q as defined above. More typically when $R^1$ is substituted, it is substituted with one or more groups (e.g. 1, 2, 3 or 4 groups) selected from halo, nitro, —CN, OH, $C_{1-6}$ alkoxy, $C_{1-6}$ hydroxyalkyl, $C_{1-6}$ alkylthio, $C_{1-6}$ haloalkyl, $C_{1-4}$ haloalkoxy, —$CO_2R'''$, —$NR'''_2$, —$SR'''$, —$S(=O)R'''$, and —$S(=O)_2R'''$, wherein each $R'''$ is independently selected from H and $C_{1-6}$ alkyl.

Still more typically, when $R^1$ is substituted, it is substituted with one or more groups (e.g. 1, 2, 3 or 4 groups) selected from halo, nitro, —CN, OH, $C_{1-4}$ alkoxy, $C_{1-4}$ hydroxyalkyl, $C_{1-4}$ alkylthio, $C_{1-4}$ haloalkyl, $C_{1-4}$ haloalkoxy, —$CO_2R'''$, —$NR'''_2$, —$SR'''$, —$S(=O)R'''$, and —$S(=O)_2R'''$, wherein each $R'''$ is independently selected from H and $C_{1-4}$ alkyl.

Preferably, when $R^1$ is substituted, it is substituted with one or more groups (e.g. 1, 2, 3 or 4 groups) selected from halo, nitro, —CN, OH. More preferably, when $R^1$ is substituted, it is substituted with one or more (e.g. 1, 2, 3 or 4, typically 3) halo atoms.

Still more preferably, when $R^1$ is substituted, it is substituted with one or more (e.g. 1, 2, 3 or 4, typically 3) fluorine atoms.

Preferably, in some embodiments, when $R^1$ is substituted it is substituted with one or more groups (e.g. 1, 2, 3 or 4 groups) selected from halo, nitro, —CN, OH. More preferably, when $R^1$ is substituted, it is substituted with one or more (e.g. 1, 2, 3 or 4, typically 3) halo atoms or one or more (e.g. 1, 2, 3 or 4, typically 1) —OH groups. Still more preferably, when $R^1$ is substituted, it is substituted with one or more (e.g. 1, 2, 3 or 4, typically 3) fluorine atoms or one or more (e.g. 1, 2, 3 or 4, typically 1) —OH groups.

Typically, $R^1$ is $C_{3-6}$ alkyl, $C_{3-6}$ alkenyl, 5- or 6-membered heterocyclyl or 5- or 6-membered heteroaryl, each of which is unsubstituted or substituted. More typically $R^1$ is $C_{3-6}$ alkyl, $C_{3-6}$ alkenyl, or 5- or 6-membered heterocyclyl each of which is unsubstituted or substituted (e.g. substituted with 1 or more halogen atoms).

Typically, in some embodiments, $R^1$ is $C_{3-6}$ alkyl, $C_{3-6}$ alkenyl, 5- or 6-membered cycloalkyl, 5- or 6-membered heterocyclyl or 5- or 6-membered heteroaryl, each of which is unsubstituted or substituted. More typically $R^1$ is $C_{3-6}$ alkyl, $C_{3-6}$ alkenyl, 5- or 6-membered cycloalkyl or 5- or 6-membered heterocyclyl each of which is unsubstituted or substituted (e.g. substituted with 1 or more groups each of which is independently selected from a halogen atom and an —OH group).

Preferably, $R^1$ is $C_{3-6}$ alkyl, or 5- or 6-membered heterocyclyl each of which is unsubstituted or substituted (e.g. substituted with 1 or more halogen atoms). More preferably $R^1$ is $C_{5-6}$ alkyl which is unsubstituted or substituted (e.g. substituted with 1, 2, 3 or 4 halogen atoms), or unsubstituted 6-membered heterocyclyl. Still more preferably $R^1$ is isopentyl or n-butyl which is unsubstituted or substituted with 3 fluorine atoms, or $R^1$ is unsubstituted tetrahydropyranyl. Most preferably $R^1$ is unsubstituted isopentyl, n-butyl which is substituted with 3 fluorine atoms, or $R^1$ is unsubstituted tetrahydropyranyl.

Preferably, in some embodiments, $R^1$ is $C_{3-6}$ alkyl, 5- or 6-membered cycloalkyl or 5- or 6-membered heterocyclyl each of which is unsubstituted or substituted (e.g. substituted with 1 or more groups each of which is independently selected from a halogen atom and an —OH group). More preferably $R^1$ is $C_{5-6}$ alkyl which is unsubstituted or substituted (e.g. substituted with 1, 2, 3 or 4 halogen atoms), unsubstituted 6-membered heterocyclyl, or substituted 6-membered cycloalkyl (e.g. substituted with 1, 2, 3 or 4 —OH groups). Still more preferably $R^1$ is unsubstituted tetrahydropyranyl, hydroxycyclohexyl, or isopentyl or n-butyl which isopentyl or n-butyl group is unsubstituted or substituted with 3 fluorine atoms. Most preferably $R^1$ is unsubstituted tetrahydropyranyl, hydroxycyclohexyl, unsubstituted isopentyl, or n-butyl which is substituted with 3 fluorine atoms.

Typically, L is a single bond or $C_{1-3}$ alkylene. Preferably, L is a single bond or $C_1$ alkylene.

Typically, Z is halo, $C_{1-6}$ haloalkyl, nitro, —CN, —$N(R^2)_2$, —$OR^2$, or —$SR^2$. More typically Z is halo, $C_{1-6}$ haloalkyl (e.g. $C_{1-4}$ haloalkyl, $C_{1-2}$ haloalkyl or $C_1$ haloalkyl), —$N(R^2)_2$ or —$OR^2$. Still more typically Z is —$N(R^2)_2$, —$OR^2$, a halogen atom or $C_{1-6}$ haloalkyl. Preferably Z is halo or —$N(R^2)_2$. More preferably Z is fluoro, chloro, $NH_2$, $NHCH_3$, or $N(CH_3)_2$. Still more preferably Z is chloro or $NH_2$.

Typically, when $R^2$ is a substituted alkyl, alkenyl or alkynyl group, said alkyl, alkenyl or alkynyl group is substituted with one or more groups (e.g. 1, 2, 3 or 4 groups) selected from halo, nitro, —CN, OH, $C_{1-4}$ alkoxy, $C_{1-4}$ hydroxyalkyl, $C_{1-4}$ alkylthio, $C_{1-4}$ haloalkyl, $C_{1-4}$ haloalkoxy, —$CO_2R'''$, —$NR'''_2$, —$SR'''$, —$S(=O)R'''$, and —$S(=O)_2R'''$, wherein each $R'''$ is independently selected from H and $C_{1-4}$ alkyl. More typically, when $R^2$ is a substituted alkyl, alkenyl or alkynyl group, said alkyl, alkenyl or alkynyl group is substituted with one or more groups (e.g. 1, 2, 3 or 4 groups) selected from halo, nitro, —CN, OH.

Typically, each $R^2$ is independently hydrogen, $C_{1-4}$ alkyl, $C_{2-4}$ alkenyl or $C_{2-4}$ alkynyl, wherein said alkyl, alkenyl and alkynyl groups are unsubstituted or substituted. Preferably each $R^2$ is independently hydrogen or $C_{1-4}$ alkyl, wherein said alkyl group is unsubstituted or substituted. More preferably each $R^2$ is independently hydrogen or unsubstituted $C_{1-4}$ alkyl. Still more preferably each $R^2$ is independently hydrogen or unsubstituted methyl. Most preferably each $R^2$ is hydrogen.

Typically, m is 1.

In certain preferred embodiments, L is a direct bond and Z is a halogen atom (e.g. Z is a chlorine atom). In other preferred embodiments, L is a $C_1$ alkylene group and Z is $—N(R_2)_2$ (e.g. Z is $—NH_2$).

In one particularly preferred embodiment of the compounds of the invention, in formula (I):
one of X and Y is an N atom or C substituted with a fluorine atom, and the other is CH;
$R^1$ is $C_{5-6}$ alkyl, which is unsubstituted or substituted with one, two, three or four fluorine atoms, or unsubstituted tetrahydropyan
m is 1
L is a single bond or $C_1$ alkylene; and
Z is $NH_2$ or a chlorine atom.

In another particularly preferred embodiment of the compounds of the invention, in formula (I):
one of X and Y is an N atom or C substituted with a fluorine atom, and the other is CH;
$R^1$ is $C_{5-6}$ alkyl, which is unsubstituted or substituted with one, two, three or four fluorine atoms, $R^1$ is cyclohexyl which is unsubstituted or substituted with one or two —OH groups, or $R^1$ is unsubstituted tetrahydropyan;
m is 1
L is a single bond or $C_1$ alkylene; and
Z is $NH_2$ or a chlorine atom.

Specific compounds of the invention include:
1'-{[5-(aminomethyl)-1-(4,4,4-trifluorobutyl)-1H-1,3-benzodiazol-2-yl]methyl}-6'-fluoro-1',2'-dihydrospiro[cyclopropane-1,3'-indole]-2'-one;
1'-((5-(aminomethyl)-1-(4,4,4-trifluorobutyl)-1H-benzo[d]imidazol-2-yl)methyl)spiro[cyclopropane-1,3'-pyrrolo[2,3-b]pyridin]-2'(1'H)-one;
1'-((5-chloro-1-(tetrahydro-2H-pyran-4-yl)-1H-benzo[d]imidazol-2-yl)methyl)spiro[cyclopropane-1,3'-pyrrolo[2,3-c]pyridin]-2'(1'H)-one;
1'-((5-(aminomethyl)-1-isopentyl-1H-benzo[d]imidazol-2-yl)methyl)spiro[cyclopropane-1,3'-pyrrolo[2,3-b]pyridin]-2'(1'H)-one;
1'-((5-(aminomethyl)-1-isopentyl-1H-benzo[d]imidazol-2-yl)methyl)spiro[cyclopropane-1,3'-pyrrolo[2,3-c]pyridin]-2'(1'H)-one; and
1'-((5-(aminomethyl)-1-(tetrahydro-2H-pyran-4-yl)-1H-benzo[d]imidazol-2-yl)methyl)-6'-fluorospiro[cyclopropane-1,3'-indolin]-2'-one;
and the pharmaceutically acceptable salts thereof.

In certain embodiments, specific compounds of the invention include:
1'-{[5-(aminomethyl)-1-(4,4,4-trifluorobutyl)-1H-1,3-benzodiazol-2-yl]methyl}-6'-fluoro-1',2'-dihydrospiro[cyclopropane-1,3'-indole]-2'-one;
1'-((5-(aminomethyl)-1-(4,4,4-trifluorobutyl)-1H-benzo[d]imidazol-2-yl)methyl)spiro[cyclopropane-1,3'-pyrrolo[2,3-b]pyridin]-2'(1'H)-one;
1'-((5-chloro-1-(tetrahydro-2H-pyran-4-yl)-1H-benzo[d]imidazol-2-yl)methyl)spiro[cyclopropane-1,3'-pyrrolo[2,3-c]pyridin]-2'(1'H)-one;
1'-((5-(aminomethyl)-1-isopentyl-1H-benzo[d]imidazol-2-yl)methyl)spiro[cyclopropane-1,3'-pyrrolo[2,3-b]pyridin]-2'(1'H)-one;
1'-((5-(aminomethyl)-1-isopentyl-1H-benzo[d]imidazol-2-yl)methyl)spiro[cyclopropane-1,3'-pyrrolo[2,3-c]pyridin]-2'(1'H)-one; and
1'-((5-(aminomethyl)-1-(tetrahydro-2H-pyran-4-yl)-1H-benzo[d]imidazol-2-yl)methyl)-6'-fluorospiro[cyclopropane-1,3'-indolin]-2'-one;
1'-((5-(Aminomethyl)-1-((1R,4R)-4-hydroxycyclohexyl)-1H-benzo[d]imidazol-2-yl)methyl)-6'-fluorospiro[cyclopropane-1,3'-indolin]-2'-one
and the pharmaceutically acceptable salts thereof.

Preferred compounds of the invention include 1'-{[5-(aminomethyl)-1-(4,4,4-trifluorobutyl)-1H-1,3-benzodiazol-2-yl]methyl}-6'fluoro-1',2'-dihydrospiro[cyclopropane-1,3'-indole]-2'-one.

In some embodiments, when -L-Z is $C_{1-6}$ alkoxy, halogen, trifluoromethyl or cyano, $R^1$ is not $C_{1-6}$ alkyl substituted by $R^{100}$,
wherein $R^{100}$ is selected from $C_{1-6}$ alkylsulfonylphenyl, thietan-3-yl, dioxothietan-3-yl, oxetan-3-yl, aminooxetan-3-yl, hydroxy, $C_{1-6}$ alkylsufinyl, trifluoromethyl-$C_{1-6}$alkylene-aminocarbonyloxy,

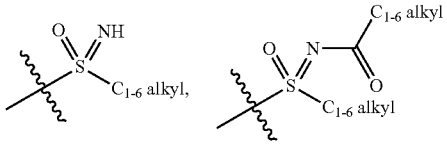

and $SO_2R^{108}$;
wherein $R^{108}$ is $C_{1-6}$ alkyl, cycloalkyl, $C_{1-6}$ alkylcarbonylamino, $C_{1-6}$ alkylamino di-$C_{1-6}$ alkylamino, amino, morpholinyl, pyrrolidinyl, piperazinyl,

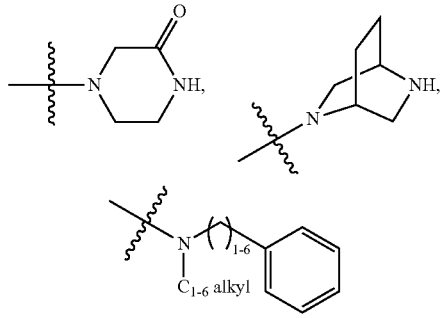

or $C_{1-6}$ alkylene-$COR^{109}$; wherein $R^{109}$ is $C_{1-6}$ alkoxy, amino, hydroxy, cycloalkylsulfonylamino, cycloalkylsulfonylamino($C_{1-6}$ alkyl) $C_{1-6}$ alkylsulfonylamino($C_{1-6}$ alkyl), or $C_{2-6}$ alkyl-$NR^{110}R^{111}$;
wherein $R^{110}$ is hydrogen, $R^{111}$ is hydrogen, $C_{1-6}$ alkoxycarbonyl, $C_{1-6}$ alkylcarbonyl, $C_{1-6}$ alkylsulfonyl, or hydroxy-$C_{1-6}$ alkyl, or $R^{110}$ and $R^{111}$, together with the nitrogen atom to which they are attached, form

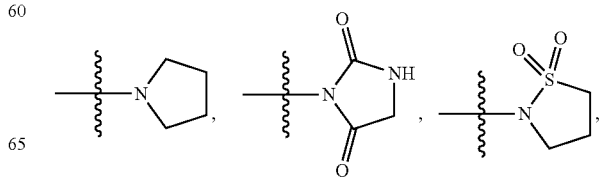

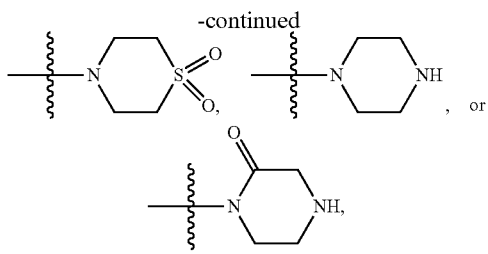

which is unsubstituted or substituted by hydroxy, $C_{1-6}$ alkylcarbonyl or $C_{1-6}$ alkylsulfonyl.

In some embodiments, when -L-Z is $C_{1-6}$ alkoxy, halogen, trifluoromethyl or cyano, $R^1$ is $C_{2-6}$ alkenyl, $C_{2-6}$ alkynyl, 5- to 10-membered heterocyclyl or 5- to 12-membered heteroaryl, each of which is unsubstituted or substituted (e.g. substituted by one or more groups Q as defined above), or $R^1$ is $C_{1-6}$ alkyl which is unsubstituted or substituted by one or more groups (e.g. 1, 2, 3 or 4 groups) selected from halo, nitro, —CN, $C_{1-6}$ alkoxy, $C_{1-6}$ alkylthio, $C_{1-6}$ haloalkyl, $C_{1-4}$ haloalkoxy, —$CO_2R'''$, —$NR'''_2$, —$SR'''$, $C_3-C_{10}$ cycloalkyl, 5 to 10-membered heterocyclyl, or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl. Typically, in such embodiments, when -L-Z is $C_{1-6}$ alkoxy, halogen, trifluoromethyl or cyano, $R^1$ is 5- to 10-membered heterocyclyl or 5- to 12-membered heteroaryl, each of which is unsubstituted or substituted (e.g. substituted by one or more groups Q as defined above), or $R^1$ is a $C_{1-6}$ alkyl, $C_{2-6}$ alkenyl or $C_{2-6}$ alkynyl group, which alkyl, alkenyl or alkynyl group is unsubstituted or substituted by one or more groups (e.g. 1, 2, 3 or 4 groups) selected from halo, nitro, —CN, $C_{1-6}$ alkoxy, $C_{1-6}$ alkylthio, $C_{1-6}$ haloalkyl, $C_{1-4}$ haloalkoxy, —$CO_2R'''$, —$NR'''_2$, —$SR'''$, $C_3-C_{10}$ cycloalkyl, 5 to 10-membered heterocyclyl, or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

In some embodiments, -L-Z is not $C_{1-6}$ alkoxy, halogen, trifluoromethyl or cyano. For example, in some embodiments Z is nitro, —$N(R^2)_2$, —$SR^2$, —$S(=O)R^2$, or —$S(=O)_2R^2$, and L is as defined above.

In some embodiments, $R^1$ is not $C_{1-6}$ alkyl substituted by $R^{100}$, wherein $R^{100}$ is as defined above. For example, in some embodiments, $R^1$ is $C_{2-6}$ alkenyl, $C_{2-6}$ alkynyl, 5- to 10-membered heterocyclyl or 5- to 12-membered heteroaryl, each of which is unsubstituted or substituted (e.g. substituted by one or more groups Q as defined above), or $R^1$ is $C_{1-6}$ alkyl which is unsubstituted or substituted by one or more groups (e.g. 1, 2, 3 or 4 groups) selected from halo, nitro, —CN, $C_{1-6}$ alkoxy, $C_{1-6}$ alkylthio, $C_{1-6}$ haloalkyl, $C_{1-4}$ haloalkoxy, —$CO_2R'''$, —$NR'''_2$, —$SR'''$, $C_3-C_{10}$ cycloalkyl, 5 to 10-membered heterocyclyl, or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

In some embodiments, when -L-Z is chloro, $R^1$ is not $C_{1-6}$ alkyl substituted by —$S(=O)_2R'''$, wherein R''' is H or $C_{1-4}$ alkyl.

In some embodiments, when -L-Z is chloro, $R^1$ is $C_{2-6}$ alkenyl, $C_{2-6}$ alkynyl, 5- to 10-membered heterocyclyl or 5- to 12-membered heteroaryl, each of which is unsubstituted or substituted (e.g. substituted by one or more groups Q as defined above), or $R^1$ is $C_{1-6}$ alkyl which is unsubstituted or substituted by one or more groups (e.g. 1, 2, 3 or 4 groups) selected from halo, nitro, —CN, OH, $C_{1-6}$ alkoxy, $C_{1-6}$ hydroxyalkyl, $C_{1-6}$ alkylthio, $C_{1-6}$ haloalkyl, $C_{1-4}$ haloalkoxy, —$CO_2R'''$, —$NR'''_2$, —$SR'''$, —$S(=O)R'''$, $C_3-C_{10}$ cycloalkyl, 5 to 10-membered heterocyclyl, 5- to 12-membered aryl or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

In some embodiments, -L-Z is not chloro. For example, in some embodiments, Z is F, Br, I, $C_{1-6}$ haloalkyl, nitro, —CN, —$N(R^2)_2$, —$OR^2$, —$SR^2$, —$S(=O)R^2$, or —$S(=O)_2R^2$, and L is as defined above. Typically, in such embodiments, Z is $C_{1-6}$ haloalkyl, nitro, —CN, —$N(R^2)_2$, —$OR^2$, —$SR^2$, —$S(=O)R^2$, or —$S(=O)_2R^2$, and L is as defined above.

In some embodiments, $R^1$ is not $C_{1-6}$ alkyl substituted by —$S(=O)_2R'''$, wherein R''' is H or $C_{1-4}$ alkyl. For example, in some embodiments, $R^1$ is $C_{2-6}$ alkenyl, $C_{2-6}$ alkynyl, 5- to 10-membered heterocyclyl or 5- to 12-membered heteroaryl, each of which is unsubstituted or substituted (e.g. substituted by one or more groups Q as defined above), or $R^1$ is $C_{1-6}$ alkyl which is unsubstituted or substituted by one or more groups (e.g. 1, 2, 3 or 4 groups) selected from halo, nitro, —CN, OH, $C_{1-6}$ alkoxy, $C_{1-6}$ hydroxyalkyl, $C_{1-6}$ alkylthio, $C_{1-6}$ haloalkyl, $C_{1-4}$ haloalkoxy, —$CO_2R'''$, —$NR'''_2$, —$SR'''$, —$S(=O)R'''$, $C_3-C_{10}$ cycloalkyl, 5 to 10-membered heterocyclyl, 5- to 12-membered aryl or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl. Typically, in such embodiments, $R^1$ is 5- to 10-membered heterocyclyl or 5- to 12-membered heteroaryl, each of which is unsubstituted or substituted (e.g. substituted by one or more groups Q as defined above), or $R^1$ is $C_{1-6}$ alkyl, $C_{2-6}$ alkenyl, or $C_{2-6}$ alkynyl which alkyl, alkenyl or alkynyl group is unsubstituted or substituted by one or more groups (e.g. 1, 2, 3 or 4 groups) selected from halo, nitro, —CN, OH, $C_{1-6}$ alkoxy, $C_{1-6}$ hydroxyalkyl, $C_{1-6}$ alkylthio, $C_{1-6}$ haloalkyl, $C_{1-4}$ haloalkoxy, —$CO_2R'''$, —$NR'''_2$, —$SR'''$, —$S(=O)R'''$, $C_3-C_{10}$ cycloalkyl, 5 to 10-membered heterocyclyl, 5- to 12-membered aryl or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

In some embodiments, when -L-Z is halo, $R^1$ is not azetidinyl, which is unsubstituted or substituted by $C_{1-6}$ alkyl sulfonyl; $C_{1-6}$ alkoxycarbonylpyrrolidinyl; $C_{1-6}$ alkylcarbonylpyrrolidinyl; cycloalkyl, which is unsubstituted or substituted by $C_{1-6}$ alkyl, $C_{1-6}$ alkyl sulfonyl, carboxy, halogen or hydroxy; dioxo-tetrahydrothiophenyl, which is unsubstituted or substituted by $C_{1-6}$ alkyl; dioxo-tetrahydrothiopyranyl; dioxo-thietanyl; oxo-thietanyl; oxo-pyrrolidinyl, which is unsubstituted or substituted by $C_{1-6}$ alkyl; oxetanyl; oxopiperidinyl; piperidinyl; tetrahydrofuranyl; tetrahydropyranyl;

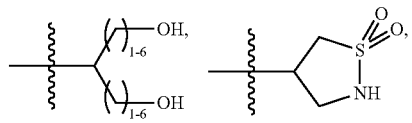

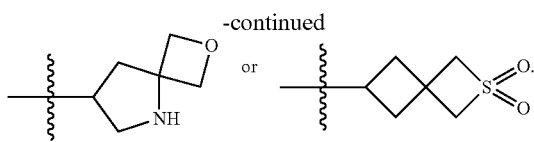

In some embodiments, when -L-Z is halo, $R^1$ is not alkyl substituted by one or more hydroxyl groups, $R^1$ is not cycloalkyl, and $R^1$ is not heterocyclyl. For example, in some embodiments, when -L-Z is halo, $R^1$ is $C_{2-6}$ alkenyl, $C_{2-6}$ alkynyl, or 5- to 12-membered heteroaryl, each of which is unsubstituted or substituted (e.g. substituted by one or more groups Q as defined above); or $R^1$ is $C_{1-6}$ alkyl which is unsubstituted or substituted by one or more (e.g. 1, 2, 3 or 4) groups selected from halo, nitro, —CN, $C_{1-6}$ alkoxy, $C_{1-6}$ alkylthio, $C_{1-6}$ haloalkyl, $C_{1-4}$ haloalkoxy, —CO$_2$R''', —NR'''$_2$, —SR''', —S(=O)R''', —S(=O)$_2$R''', $C_3$-$C_{10}$ cycloalkyl, 5 to 10-membered heterocyclyl, 5- to 12-membered aryl or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl. Typically in these embodiments, when -L-Z is halo, $R^1$ is 5- to 12-membered heteroaryl, which is unsubstituted or substituted (e.g. substituted by one or more groups Q as defined above); or $R^1$ is $C_{1-6}$ alkyl $C_{2-6}$ alkenyl, or $C_{2-6}$ alkynyl, each of which alkyl, alkenyl or alkynyl groups is unsubstituted or substituted by one or more (e.g. 1, 2, 3 or 4) groups selected from halo, nitro, —CN, $C_{1-6}$ alkoxy, $C_{1-6}$ alkylthio, $C_{1-6}$ haloalkyl, $C_{1-4}$ haloalkoxy, —CO$_2$R''', —NR'''$_2$, —SR''', —S(=O)R''', —S(=O)$_2$R''', $C_3$-$C_{10}$ cycloalkyl, 5 to 10-membered heterocyclyl, 5- to 12-membered aryl or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

In some embodiments, -L-Z is not halo. For example, in some embodiments, Z is $C_{1-6}$ haloalkyl, nitro, —CN, —N(R$^2$)$_2$, —OR$^2$, —SR$^2$, —S(=O)R$^2$, or —S(=O)$_2$R$^2$, and L is as defined above.

In some embodiments, $R^1$ is not alkyl substituted by one or more hydroxyl groups, $R^1$ is not cycloalkyl, and $R^1$ is not heterocyclyl. For example, in some embodiments, $R^1$ is $C_{2-6}$ alkenyl, $C_{2-6}$ alkynyl, or 5- to 12-membered heteroaryl, each of which is unsubstituted or substituted (e.g. substituted by one or more groups Q as defined above); or $R^1$ is $C_{1-6}$ alkyl which is unsubstituted or substituted by one or more (e.g. 1, 2, 3 or 4) groups selected from halo, nitro, —CN, $C_{1-6}$ alkoxy, $C_{1-6}$ alkylthio, $C_{1-6}$ haloalkyl, $C_{1-4}$ haloalkoxy, —CO$_2$R''', —NR'''$_2$, —SR''', —S(=O)R''', —S(=O)$_2$R''', $C_3$-$C_{10}$ cycloalkyl, 5 to 10-membered heterocyclyl, 5- to 12-membered aryl or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl. Typically in these embodiments, $R^1$ is 5- to 12-membered heteroaryl which is unsubstituted or substituted (e.g. substituted by one or more groups Q as defined above); or $R^1$ is $C_{1-6}$ alkyl $C_{2-6}$ alkenyl, or $C_{2-6}$ alkynyl, each of which alkyl, alkenyl or alkynyl groups is unsubstituted or substituted by one or more (e.g. 1, 2, 3 or 4) groups selected from halo, nitro, —CN, $C_{1-6}$ alkoxy, $C_{1-6}$ alkylthio, $C_{1-6}$ haloalkyl, $C_{1-4}$ haloalkoxy, —CO$_2$R''', —NR'''$_2$, —SR''', —S(=O)R''', —S(=O)$_2$R''', $C_3$-$C_{10}$ cycloalkyl, 5 to 10-membered heterocyclyl, 5- to 12-membered aryl or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

In some embodiments, when -L-Z is chloro, $R^1$ is not dioxidotetrahydrothiopyranyl, tetrahydropyranyl, oxopyrrolidinyl, oxopiperidinyl, tetrahydrofuranyl, tertbutoxycarbonylpyrrolidinyl, dihydroxypropanyl, dioxidotetrahydrothiophenyl, methyloxopyrrolidinyl, ethyloxopyrrolidinyl, piperidinyl, 2-methylpropanoylpyrrolidinyl, propanoylpyrrolidinyl, dimethyldioxidotetrahydrothiophenyl, dioxidothiazolidinyl, oxaazaspiro[3.4]octyl, cyclopentyl, difluorocyclobutyl, hydroxycyclohexyl, hydroxycyclopentyl, difluorocyclopentyl, cyclohexanecarboxylic acid, (hydroxyl)(methyl)cyclobutyl, or hydroxycyclobutyl. In examples of these embodiments, when -L-Z is chloro, $R^1$ is not heterocyclyl, $R^1$ is not cycloalkyl, and $R^1$ is not alkyl substituted by one or more hydroxyl groups. Typically, in these embodiments, when -L-Z is chloro, $R^1$ is 5- to 12-membered heteroaryl which is unsubstituted or substituted (e.g. substituted by one or more groups Q as defined above); or $R^1$ is $C_{1-6}$ alkyl $C_{2-6}$ alkenyl, or $C_{2-6}$ alkynyl, each of which alkyl, alkenyl or alkynyl groups is unsubstituted or substituted with one or more (e.g. 1, 2, 3 or 4) groups selected from halo, nitro, —CN, $C_{1-6}$ alkoxy, $C_{1-6}$ alkylthio, $C_{1-6}$ haloalkyl, $C_{1-4}$ haloalkoxy, —CO$_2$R''', —NR'''$_2$, —SR''', —S(=O)R''', —S(=O)$_2$R''', $C_3$-$C_{10}$ cycloalkyl, 5 to 10-membered heterocyclyl, 5- to 12-membered aryl or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

In some embodiments $R^1$ is not dioxidotetrahydrothiopyranyl, tetrahydropyranyl, oxopyrrolidinyl, oxopiperidinyl, tetrahydrofuranyl, tertbutoxycarbonylpyrrolidinyl, dihydroxypropanyl, dioxidotetrahydrothiophenyl, methyloxopyrrolidinyl, ethyloxopyrrolidinyl, piperidinyl, 2-methylpropanoylpyrrolidinyl, propanoylpyrrolidinyl, dimethyldioxidotetrahydrothiophenyl, dioxidothiazolidinyl, oxaazaspiro[3.4]octyl, cyclopentyl, difluorocyclobutyl, hydroxycyclohexyl, hydroxycyclopentyl, difluorocyclopentyl, cyclohexanecarboxylic acid, (hydroxyl)(methyl)cyclobutyl, or hydroxycyclobutyl.

In some embodiments, when -L-Z is halo, $R^1$ is not pyridine substituted by one group, which group is selected from $C_{1-6}$ alkylsulfonyl, $C_{1-6}$ alkoxy, —CN and hydroxyl.

In some embodiments, when -L-Z is halo, $R^1$ is $C_{1-6}$ alkyl, $C_{2-6}$ alkenyl, $C_{2-6}$ alkynyl, or 3- to 10-membered cycloalkyl or 5- to 10-membered heterocyclyl, each of which is unsubstituted or substituted (e.g. substituted by one or more groups Q as defined above); or 5- to 12-membered heteroaryl which is unsubstituted or substituted by one or more groups (e.g. 1, 2, 3 or 4 groups) selected from halo, nitro, $C_{1-6}$ hydroxyalkyl, $C_{1-6}$ alkylthio, $C_{1-6}$ haloalkyl, $C_{1-4}$ haloalkoxy, —CO$_2$R''', —NR'''$_2$, —SR''', —S(=O)R''', $C_3$-$C_{10}$ cycloalkyl, 5 to 10-membered heterocyclyl, 5- to 12-membered aryl or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

In some embodiments, $R^1$ is $C_{1-6}$ alkyl, $C_{2-6}$ alkenyl, $C_{2-6}$ alkynyl, 3- to 10-membered cycloalkyl or 5- to 10-membered heterocyclyl, each of which is unsubstituted or substituted (e.g. substituted by one or more groups Q as defined above); or 5- to 12-membered heteroaryl which is unsubstituted or substituted by one or more groups (e.g. 1, 2, 3 or 4 groups) selected from halo, nitro, $C_{1-6}$ hydroxyalkyl, $C_{1-6}$ alkylthio, $C_{1-6}$ haloalkyl, $C_{1-4}$ haloalkoxy, —CO$_2$R''', —NR'''$_2$, —SR''', —S(=O)R''', $C_3$-$C_{10}$ cycloalkyl, 5 to 10-membered heterocyclyl, 5- to 12-membered aryl or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

In some embodiments, when -L-Z is chloro, $R^1$ is not pyridine substituted with a —CN, methylsulfonyl, ethylsulfonyl, methoxy, or hydroxy group. For example, in some embodiments, when -L-Z is chloro, $R^1$ is $C_{1-6}$ alkyl, $C_{2-6}$ alkenyl, $C_{2-6}$ alkynyl, 3- to 10-membered cycloalkyl or 5- to 10-membered heterocyclyl, each of which is unsubstituted or substituted (e.g. substituted by one or more groups Q as defined above); or 5- to 12-membered heteroaryl which is unsubstituted or substituted by one or more groups (e.g. 1, 2, 3 or 4 groups) selected from halo, nitro, $C_{1-6}$ hydroxyalkyl, $C_{1-6}$ alkylthio, $C_{1-6}$ haloalkyl, $C_{1-4}$ haloalkoxy, —CO$_2$R''', —NR'''$_2$, —SR''', —S(=O)R''', $C_3$-$C_{10}$ cycloalkyl, 5 to 10-membered heterocyclyl, 5- to 12-membered aryl or 5- to 12-membered heteroaryl, wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

In some embodiments, when -L-Z is $C_{1-6}$ alkoxy, halogen, trifluoromethyl or cyano, $R^1$ is a $C_{1-6}$ alkyl, $C_{2-6}$ alkenyl or $C_{2-6}$ alkynyl group, which alkyl, alkenyl or alkynyl group is unsubstituted or substituted by one or more groups (e.g. 1, 2, 3 or 4 groups) selected from halo, nitro, —CN, $C_{1-6}$ alkoxy, $C_{1-6}$ alkylthio, $C_{1-6}$ haloalkyl, $C_{1-4}$ haloalkoxy, —CO$_2$R''', —NR'''$_2$, —SR''', $C_3$-$C_{10}$ cycloalkyl, 5 to 10-membered heterocyclyl, or 5- to 12-membered heteroaryl; or $R^1$ is a 5- to 12-membered heteroaryl, which is unsubstituted or substituted by one or more groups (e.g. 1, 2, 3 or 4 groups) selected from halo, nitro, $C_{1-6}$ hydroxyalkyl, $C_{1-6}$ alkylthio, $C_{1-6}$ haloalkyl, $C_{1-4}$ haloalkoxy, —CO$_2$R''', —NR'''$_2$, —SR''', —S(=O)R''', $C_3$-$C_{10}$ cycloalkyl, 5 to 10-membered heterocyclyl, 5- to 12-membered aryl or 5- to 12-membered heteroaryl; wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

In some embodiments $R^1$ is a $C_{1-6}$ alkyl, $C_{2-6}$ alkenyl or $C_{2-6}$ alkynyl group, which alkyl, alkenyl or alkynyl group is unsubstituted or substituted by one or more groups (e.g. 1, 2, 3 or 4 groups) selected from halo, nitro, —CN, $C_{1-6}$ alkoxy, $C_{1-6}$ alkylthio, $C_{1-6}$ haloalkyl, $C_{1-4}$ haloalkoxy, —CO$_2$R''', —NR'''$_2$, —SR''', $C_3$-$C_{10}$ cycloalkyl, 5 to 10-membered heterocyclyl, or 5- to 12-membered heteroaryl; or $R^1$ is a 5- to 12-membered heteroaryl, which is unsubstituted or substituted by one or more groups (e.g. 1, 2, 3 or 4 groups) selected from halo, nitro, $C_{1-6}$ hydroxyalkyl, $C_{1-6}$ alkylthio, $C_{1-6}$ haloalkyl, $C_{1-4}$ haloalkoxy, —CO$_2$R''', —NR'''$_2$, —SR''', —S(=O)R''', $C_3$-$C_{10}$ cycloalkyl, 5 to 10-membered heterocyclyl, 5- to 12-membered aryl or 5- to 12-membered heteroaryl; wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

In some embodiments, when Z is Cl, $R^1$ is $C_{1-6}$ alkyl, $C_{2-6}$ alkenyl, or $C_{2-6}$ alkynyl which alkyl, alkenyl or alkynyl group is unsubstituted or substituted by one or more groups (e.g. 1, 2, 3 or 4 groups) selected from halo, nitro, —CN, $C_{1-6}$ alkoxy, $C_{1-6}$ alkylthio, $C_{1-6}$ haloalkyl, $C_{1-4}$ haloalkoxy, —CO$_2$R''', —NR'''$_2$, —SR''', —S(=O)R''', $C_3$-$C_{10}$ cycloalkyl, 5 to 10-membered heterocyclyl, 5- to 12-membered aryl or 5- to 12-membered heteroaryl; or $R^1$ is 5- to 12-membered heteroaryl which is unsubstituted or substituted by one or more groups (e.g. 1, 2, 3 or 4 groups) selected from halo, nitro, $C_{1-6}$ hydroxyalkyl, $C_{1-6}$ alkylthio, $C_{1-6}$ haloalkyl, $C_{1-4}$ haloalkoxy, —CO$_2$R''', —NR'''$_2$, —SR''', —S(=O)R''', $C_3$-$C_{10}$ cycloalkyl, 5 to 10-membered heterocyclyl, 5- to 12-membered aryl or 5- to 12-membered heteroaryl; wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

In some embodiments, $R^1$ is $C_{1-6}$ alkyl, $C_{2-6}$ alkenyl, or $C_{2-6}$ alkynyl which alkyl, alkenyl or alkynyl group is unsubstituted or substituted by one or more groups (e.g. 1, 2, 3 or 4 groups) selected from halo, nitro, —CN, $C_{1-6}$ alkoxy, $C_{1-6}$ alkylthio, $C_{1-6}$ haloalkyl, $C_{1-4}$ haloalkoxy, —CO$_2$R''', —NR'''$_2$, —SR''', —S(=O)R''', $C_3$-$C_{10}$ cycloalkyl, 5 to 10-membered heterocyclyl, 5- to 12-membered aryl or 5- to 12-membered heteroaryl; or $R^1$ is 5- to 12-membered heteroaryl which is unsubstituted or substituted by one or more groups (e.g. 1, 2, 3 or 4 groups) selected from halo, nitro, $C_{1-6}$ hydroxyalkyl, $C_{1-6}$ alkylthio, $C_{1-6}$ haloalkyl, $C_{1-4}$ haloalkoxy, —CO$_2$R''', —NR'''$_2$, —SR''', —S(=O)R''', $C_3$-$C_{10}$ cycloalkyl, 5 to 10-membered heterocyclyl, 5- to 12-membered aryl or 5- to 12-membered heteroaryl; wherein each R''' is independently selected from H, $C_{1-6}$ alkyl, $C_{3-10}$ cycloalkyl, 5 to 10-membered heterocyclyl, 5- to 12-membered aryl and 5- to 12-membered heteroaryl.

The compounds of the invention may contain asymmetric or chiral centres, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Compounds of Formula (I) containing one or more chiral centre may be used in enantiomerically or diastereoisomerically pure form, or in the form of a mixture of isomers.

The present invention embraces all geometric and positional isomers of compounds of the invention as defined above. For example, if a compound of the invention incorporates a double bond or a fused ring, the cis- and trans-forms, as well as mixtures thereof, are embraced within the scope of the invention. Both the single positional isomers and mixture of positional isomers are also within the scope of the present invention.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol tautomerizations. Valence tautomers include interconversions by reorganization of some of the bonding electrons.

Compounds of the invention can be prepared according to the reaction schemes taught in WO 2013/068769 or by analogy thereto. Compounds of the invention may also be prepared by synthetic methods described in the Examples that follow, or by analogy with such methods.

A benzimidazole of formula (I) can be converted into a pharmaceutically acceptable salt thereof, and a salt can be converted into the free compound, by conventional methods.

For instance, a benzimidazole of formula (I) can be contacted with a pharmaceutically acceptable acid to form a pharmaceutically acceptable salt. A pharmaceutically acceptable salt is a salt with a pharmaceutically acceptable acid or base.

Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases such as alkyl amines, aralkyl amines and heterocyclic amines.

Compounds of the present invention have been found in biological tests to be inhibitors of respiratory syncytial virus (RSV). The compounds are therefore therapeutically useful. Accordingly, the present invention further provides a compound which is a benzimidazole of formula (I), as defined above, or a pharmaceutically acceptable salt thereof, for use in a method of treating the human or animal body by therapy. The invention also provides a compound of the invention as defined above for use in a method treating or preventing an RSV infection. Still further, the present invention provides the use of a compound of the invention as defined above in the manufacture of a medicament for use in treating or preventing an RSV infection. A subject suffering from or susceptible to an RSV infection may thus be treated by a method comprising the administration thereto of a compound of the invention as defined above. The condition of the subject may thereby be improved or ameliorated.

The RSV infection is typically a respiratory tract infection. The RSV infection may be an infection in a child, for instance a child under ten years of age or an infant under two years of age. In one embodiment the invention provides a compound as defined above for use in treating or preventing an RSV infection in paediatric patients. Alternatively the infection may be an infection in a mature or elderly adult, for instance an adult over 60 years of age, an adult over 70 years of age, or an adult over 80 years of age. The invention further provides a compound for use in treating or preventing an RSV infection in geriatric patients.

The RSV infection may be an infection in an immunocompromised individual or an individual suffering from COPD or CHF. In another embodiment, the RSV infection is an infection in a non-compromised individual, for instance an individual who is otherwise healthy.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection, infusion, or by inhalation or nebulisation. The compound is preferably given by oral administration.

The dosage depends on a variety of factors including the age, weight and condition of the patient and the route of administration. Daily dosages can vary within wide limits and will be adjusted to the individual requirements in each particular. Typically, however, the dosage adopted for each route of administration when a compound is administered alone to adult humans is 0.0001 to 650 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A unit dose form such as a tablet or a capsule will usually contain 1-250 mg of active ingredient. For example, a compound of formula (I) could be administered to a human patient at a dose of between 100-250 mg either once a day, twice or three times a day.

For example, a compound of formula (I) could be administered to a human patient at a dose of between 100-250 mg either once a day, twice or three times a day.

The compounds of formula (I) and pharmaceutically acceptable salts thereof may be used on their own. Alternatively, they may be administered in the form of a pharmaceutical composition. The present invention therefore also provides a pharmaceutical composition comprising a compound of formula (I) or a pharmaceutically acceptable salt thereof as hereinbefore defined, in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The invention further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

The compounds of the invention may be administered in a variety of dosage forms. Thus, they can be administered orally, for example as tablets, troches, lozenges, aqueous or oily suspensions, solutions, dispersible powders or granules. The compounds of the invention may also be administered parenterally, whether subcutaneously, intravenously, intramuscularly, intrasternally, transdermally, by infusion techniques or by inhalation or nebulisation. The compounds may also be administered as suppositories.

Solid oral forms of the pharmaceutical composition of the invention may contain, together with the active compound, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, arabic gums, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulfates; and, in general, non toxic and pharmacologically inactive substances used in pharmaceutical formulations. Such pharmaceutical preparations may be manufactured in known manner, for example, by means of mixing, granulating, tableting, sugar coating, or film coating processes.

Liquid dispersions for oral administration may be syrups, emulsions and suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride. Further suitable carriers for suspensions include sterile water, hydroxypropylmethyl cellulose (HPMC), polysorbate 80, polyvinylpyrrolidone (PVP), aerosol AOT (i.e. sodium 1,2-bis(2-ethylhexoxycarbonyl)ethanesulphonate), pluronic F127 and/or captisol (i.e. sulfobutylether-beta-cyclodextrin).

The compounds of the invention may, for example, be formulated as aqueous suspensions in a carrier selected from:

(i) 0.5% w/v hydroxypropylmethyl cellulose (HPMC)/ 0.1% w/v polysorbate 80;

(ii) 0.67% w/v polyvinylpyrrolidone (PVP)/0.33% w/v aerosol AOT (sodium 1,2-bis(2-ethylhexoxycarbonyl)ethanesulphonate);

(iii) 1% w/v pluronic F 127; and (iv) 0.5% w/v polysorbate 80.

The carriers may be prepared by standard procedures known to those of skill in the art. For example, each of the carriers (i) to (iv) may be prepared by weighing the required amount of excipient into a suitable vessel, adding approximately 80% of the final volume of water and magnetically stirring until a solution is formed. The carrier is then made up to volume with water. The aqueous suspensions of compounds of formula I may be prepared by weighing the required amount of a compound of formula I into a suitable vessel, adding 100% of the required volume of carrier and magnetically stirring.

Solutions for injection or infusion may contain as carrier, for example, sterile water or preferably they may be in the form of sterile, aqueous, isotonic saline solutions.

The compounds of the invention may also be administered in conjunction with other compounds used for the treatment of viral infections. Thus, the invention further relates to combination therapies wherein a compound of the invention, or a pharmaceutically acceptable salt thereof, or a pharmaceutical composition or formulation comprising a compound of the invention, is administered concurrently or sequentially or as a combined preparation with another therapeutic agent or agents, for the treatment or prevention of a viral infection, particularly infection by RSV.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

Suitable therapeutic agents for use in the combination therapies include (i) RSV nucleocapsid (N)-protein inhibitors;

(ii) other RSV protein inhibitors, such as those that inhibit the phosphoprotein (P) protein and large (L) protein;

(iii) anti-RSV monoclonal antibodies, such as the F-protein antibodies;

(iv) immunomodulating toll-like receptor compounds;

(v) other respiratory virus anti-virals, such as anti-influenza and anti-rhinovirus compounds; and/or (vi) anti-inflammatory compounds.

The RSV nucleocapsid (N)-protein plays a pivotal role in viral transcription and replication, mediating the interaction between the genomic RNA and the virally encoded RNA-dependent RNA polymerase. The RSV P- and L-proteins are components of RSV's virally encoded RNA-dependent RNA polymerase.

According to a further aspect of the invention, there is provided a compound of the formula (I) or a pharmaceutically acceptable salt thereof as hereinbefore defined in combination with one or more of the therapeutic agents listed as (i) to (vi) above for use in the treatment of RSV.

The following Examples illustrate the invention. They do not however, limit the invention in any way.

EXAMPLES

Preparatory Example 1

1,3-Diethyl-2-(4-fluoro-2-nitrophenyl) propanedioate

To a solution of 1,4-difluoro-2-nitro-benzene (10.06 g, 63.23 mmol) and diethyl propanedioate (13.58 mL, 88.99 mmol) in 50 ml of dimethylformamide was added 36.4 g of cesium carbonate slowly at room temperature under a nitrogen atmosphere. The suspension was stirred for 48 h before more dimethylformamide (20 ml) and diethyl propanedioate (2 mL) was added and the mixture stirred for a further 24 h at room temperature. The reaction mixture was then concentrated under vacuum and azeotroped with n-heptane. Water (250 ml) was added and extracted with ethyl acetate (4×75 ml). The organic phase was washed with water (1×300 ml), separated, dried over magnesium sulphate, filtered and concentrated under vacuum to afford 18.9 g (99%) of the desired product as a yellow oil.

LCMS:

M/Z [M+H]+: 299.96

1H-NMR:

1H NMR (500 MHz, Chloroform-d) δ 7.79 (dd, J=8.2, 2.7 Hz, 1H), 7.63-7.51 (m, 1H), 7.44-7.33 (m, 1H), 5.27 (s, 1H), 4.27 (qd, J=7.1, 2.2 Hz, 5H), 4.21 (d, J=7.1 Hz, 1H), 3.36 (d, J=1.1 Hz, 0H), 1.34-1.25 (m, 9H).

13C-NMR:

13C NMR (126 MHz, cdcl3) δ 167.00, 166.56, 162.68, 160.67, 133.14, 133.07, 124.24, 124.20, 120.77, 120.60, 112.91, 112.70, 77.26, 77.21, 77.01, 76.75, 62.36, 61.44, 53.74, 41.66, 14.02, 13.94.

Preparatory Example 2

Ethyl 2-(4-Fluoro-2-nitrophenyl)acetate

A mixture of diethyl 2-(4-fluoro-2-nitrophenyl) propanedioate (18. g, 60.15 mmol), lithium chloride (5.1 g, 120.3 mmol) in dimethyl sulfoxide (150 mL) and water (1.08 mL, 60.15 mmol) was heated with stirring at 100° C. for 16 hours. The reaction mixture was allowed to cool to room temperature, water (100 ml) was added then the mixture extracted with ethyl acetate (150 ml). The aqueous layer was further extracted with ethyl acetate (2×75 ml) and the combined organic layers were washed with brine (100 ml), dried over magnesium sulphate, filtered and evaporated under vacuum to leave the desired product as a yellow oil (16 g, 94%). This crude product was contaminated with 20% of the starting material and was used directly in the next step.

1H NMR (500 MHz, Chloroform-d) δ 7.86 (dd, J=8.4, 2.6 Hz, 1H), 7.39-7.30 (m, 2H), 4.18 (q, J=7.1 Hz, 2H), 4.00 (s, 3H), 1.27 (t, J=7.2 Hz, 5H).

Preparatory Example 3

6-Fluoro-2,3-dihydro-1H-indol-2-one

Under an atmosphere of nitrogen, iron filings (10.22 g, 183.11 mmol) were added in portions to a solution of ethyl 2-(4-fluoro-2-nitro-phenyl)acetate from Preparatory Example 2 (13. g, 45.78 mmol) in acetic acid (200 mL). The reaction mixture was stirred at 80° C. for 48 hours. The reaction mixture was allowed to cool to room temperature, filtered through celite, washed with ethyl acetate (100 ml) and concentrated under vacuum to leave a brown solid. This was dissolved in ethyl acetate (150 ml) and washed with saturated aqueous sodium bicarbonate (2×75 ml). The organic layer was dried over magnesium sulphate and concentrated under reduced pressure. This solid was triturated with ether and filtered to give solid (4.0 g) (58%).

The filtrate was evaporated and the residue was purified by column chromatography (silica, 25 g, ethyl acetate: petroleum ether 15:85 gradient to 80:20) to afford a light yellow solid second crop (1.5 g, 22%).

1H-NMR:
1H NMR (500 MHz, DMSO-d6) δ 10.46 (s, 1H), 7.19 (dd, J=8.1, 5.7 Hz, 1H), 6.71 (ddd, J=10.3, 8.1, 2.5 Hz, 1H), 6.61 (dd, J=9.3, 2.4 Hz, 1H), 3.43 (s, 2H).

1H-NMR:
1H NMR (500 MHz, DMSO-d6) δ 10.46 (s, 1H), 7.25-7.11 (m, 1H), 6.71 (ddd, J=10.4, 8.2, 2.5 Hz, 1H), 6.61 (dd, J=9.3, 2.4 Hz, 1H), 3.43 (t, J=1.5 Hz, 2H).

Preparatory Example 4

6' Fluoro-1',2'-dihydrospiro[cyclopropane-1,3'-indole]-2'-one

To a stirred solution of 6-fluoro-2,3-dihydro-1H-indol-2-one from Preparatory Example 3 (3. g, 19.85 mmol) and diisopropylamine (5.84 mL, 41.68 mmol) in tetrahydrofuran (30 mL) under nitrogen at −40° C. was added n-butyllithium dropwise over 30 minutes (2.5M solution in n-hexane, 31.76 mL, 79.4 mmol). The mixture was warmed to 0° C. in an ice bath. To this mixture was added dropwise a solution of 1,2-dibromoethane (5.13 mL, 59.55 mmol) in THF (10 ml). The reaction mixture was then left to stir at room temperature for 48 hours as a light brown suspension. To the mixture was added carefully a saturated aqueous solution of ammonium chloride (5 ml then 200 ml). The mixture was extracted with acetic acid (4×75 ml). The organics were combined and washed with brine (1×150 ml), dried using magnesium sulphate, filtered then concentrated under vacuum to afford 4 g of an orange-light brown solid.

This material was combined with the product from a duplicate reaction then purified using flash chromatography (100 g silica, eluted with Petroleum Ether:ethyl acetate 100:0 to 40:60 gradient) to afford the desired product 6.31 g (89%).

LCMS:
M/Z [M+H]+: 178.2
1H-NMR:
1H NMR (500 MHz, Chloroform-d) δ 9.18 (s, 1H), 6.88-6.59 (m, 3H), 1.76 (m, J=4.4, 4.0 Hz, 2H), 1.53 (m, J=4.3 Hz, 2H).

Preparatory Example 5

N-[[2-(chloromethyl)-1-(4,4,4-trifluorobutyl)-1H-1,3-benzodiazol-5-yl]methyl]carbamate To a suspension of tert-butyl N-[[2-(hydroxymethyl)-1-(4,4,4-trifluorobutyl)-1H-1,3-benzodiazol-5-yl]methyl]carbamate (obtained according to the procedure set out in WO 2010/103306; 960 mg, 2.48 mmol) in tetrahydrofuran (20 mL) was added diisopropylethylamine (1.29 mL, 7.43 mmol) and this suspension was stirred under $N_2$ for 5 minutes. This suspension was cooled to 0° C. using an ice bath and methanesulfonyl chloride (0.25 mL, 3.22 mmol) was added drop-wise over 5 minutes. The reaction was allowed to warm up to room temperature by removing the ice bath and stirred under $N_2$ overnight. Water (8 ml) was added drop wise to the mixture and the solvent was removed under vacuum. Further water (60 ml) was added and the residue was extracted with ethyl acetate (1×75 ml) then (3×25 ml). The organic phases were combined and washed with citric acid solution (1×35 ml), saturated aqueous sodium bicarbonate (1×60 ml), dried over magnesium sulphate, filtered and concentrated under vacuum to afford 1.015 g of a dark gummy crude material.

Preparatory Example 6 tert-butyl N-[(2-[(6'-fluoro-2'-oxo-1',2'-dihydrospiro [cyclopropane-1,3'-indole]-1'-ylmethyl]-1-(4,4,4-trifluorobutyl)-1H-1,3-benzodiazyl)methyl]carbamate To solution of 6'-fluoro-1,2-spiro[cyclopropane-1,3'-indole]-2'-one from Preparatory Example 4 (487.44 mg, 2.75 mmol) in N,N-dimethylformamide (10 mL) at 0° C. under nitrogen was added sodium hydride (0.11 mL, 2.75 mmol) in one portion. Once added, the cold bath was removed and the cloudy solution was stirred at room temperature for 1 hour. To this mixture was added drop wise over 5 minutes at room temperature a solution of the crude N-[[2-(chloromethyl)-1-(4,4,4-trifluorobutyl)-1H-1,3-benzodiazol-5-yl]methyl]carbamate obtained in preparatory Example 5 (1015. mg, 2.5 mmol; used without further purification) in DMF (4 ml). The mixture was stirred at room temperature for 16 hours. The reaction was quenched with water (100 ml) and extracted with ethyl acetate (3×75 ml). The combined organics were washed with water (1×100 ml), brine (120 ml), then dried over magnesium sulphate and evaporated under reduced pressure. The crude oil was purified by flash column chromatography (25 g silica) eluted with petroleum ether: ethyl acetate (100:0 gradient to 0:100). Product containing fractions were evaporated under vacuum and triturated further with Petroleum ether/ethyl acetate (4:1) (10 ml), filtered and dried under vacuum to afford 1030 mg (75%) of the desired product as a beige solid.

Preparatory Examples 5 and 6 together gave a yield of 75%.

LCMS:
M/Z [M+H]+: 547.0
1H-NMR:
$^1$H NMR (500 MHz, DMSO-d$_6$) δ 7.55 (d, J=8.3 Hz, 1H), 7.45 (s, 1H), 7.34 (t, J=6.3 Hz, 1H), 7.22-7.12 (m, 2H), 7.06 (dd, J=8.2, 5.4 Hz, 1H), 6.81 (ddd, J=10.3, 8.3, 2.4 Hz, 1H), 5.29 (s, 2H), 4.35 (t, J=7.7 Hz, 2H), 4.19 (d, J=5.9 Hz, 2H), 2.33 (ddd, J=16.6, 7.8, 4.2 Hz, 2H), 1.84 (dd, J=10.2, 5.9 Hz, 2H), 1.68 (q, J=3.9, 3.4 Hz, 2H), 1.58 (q, J=4.2, 3.8 Hz, 2H), 1.38 (s, 9H).

13C-NMR:
13C NMR (126 MHz, CDCl$_3$) δ 177.08, 163.27, 161.32, 148.40, 143.05, 142.96, 142.59, 134.48, 133.84, 127.54, 125.29, 125.27, 123.52, 119.10, 119.03, 118.96, 109.63, 109.22, 109.04, 99.69, 99.46, 77.24, 77.19, 76.99, 76.73, 44.85, 42.73, 38.22, 31.23, 30.99, 28.42, 26.68, 22.65, 22.62, 22.60, 19.56.

Preparatory Example 7

Trimethyl-[2-(pyrrolo[2,3-b]pyridin-1-ylmethoxy)ethyl]silane

Sodium hydride 60% dispersion in mineral oil (1.34 g, 33.52 mmol) was added portionwise to a solution of 1H-pyrrolo[2,3-b]pyridine (3.3 g, 27.93 mmol) in N,N-dimethylformamide (25 mL) at 0 C and the reaction mixture was stirred at 0° C. for 1 hour. After that time, 2-(chloromethoxy)ethyl-trimethylsilane (5.93 mL, 33.52 mmol) was added dropwise maintaining the internal temperature of the reaction below 10° C. The reaction mixture was allowed to slowly warm up to room temperature. LCMS after 1 hr showed the reaction is complete with the expected product present at Rt=5.18 min (100-500 MW, 7 min method) m/z 249 [M+H]+. The reaction was quenched with water (200 ml) and extracted into EtOAc (200 ml). The organic layer was washed with brine (3×100 ml), dried over MgSO4, filtered and evaporated in vacuo to give the crude product as a greenish-yellow oil (8.31 g) purified by flash chromatography (Biotage, 50 g) eluting with DCM:MeOH (100:0 to 97:3) to give the desired product in two batches as a pale oil (4.13 g) and as a clear oil (3.35 g).

1H NMR (500 MHz, Chloroform-d) δ 8.35 (dd, J=4.8, 1.6 Hz, 1H), 7.94 (d, J=7.7 Hz, 1H), 7.36 (d, J=3.6 Hz, 1H), 7.11 (dd, J=7.9, 4.7 Hz, 1H), 6.54 (d, J=3.6 Hz, 1H), 5.72 (s, 2H), 3.61-3.50 (m, 2H), 0.96-0.86 (m, 2H), −0.06 (s, 9H).

Preparatory Example 8

1-(2-trimethylsilylethoxymethyl)-3H-pyrrolo[2,3-b]pyridin-2-one

A solution of trimethyl-[2-(pyrrolo[2,3-b]pyridin-1-ylmethoxy)ethyl]silane (3.36 g, 13.51 mmol) in 1,4-dioxane (30 mL) was added dropwise to a stirring suspension of pyridinium bromide perbromide (10.5 g, 32.83 mmol) in 1,4-dioxane (30 mL). The reaction mixture was stirred at room temperature for 3 hours. The reaction mixture was quenched with water (100 ml) and extracted into EtOAc (2×100 ml). The organic layer was washed with brine (2×100 ml), dried (MgSO4), filtered and evaporated in vacuo to give the expected product 3,3-dibromo-1-(2-trimethylsilylethoxymethyl)pyrrolo[2,3-b]pyridin-2-one (4.92 g) as a golden oil:

1H NMR (500 MHz, Chloroform-d) δ 8.30 (dd, J=5.2, 1.6 Hz, 1H), 7.87 (dd, J=7.4, 1.6 Hz, 1H), 7.15 (dd, J=7.4, 5.1 Hz, 1H), 5.32 (d, J=0.9 Hz, 2H), 3.77; 3.68 (m, 2H), 0.98 (dd, J=9.0, 7.6 Hz, 2H), 0.01-0.03 (m, 9H).

Zinc dust (5.85 g, 89.53 mmol) was added to a solution of 3,3-dibromo-1-(2-trimethylsilylethoxymethyl)pyrrolo[2,3-b]pyridin-2-one (3.78 g, 8.95 mmol) in tetrahydrofuran (50 mL) and ammonium chloride sat solution (15. mL, 8.95 mmol) and the reaction mixture was stirred at 20° C. for 4 hours. LCMS and TLC analysis (Pet Ether:EtOAc, 3:1) showed complete reaction.

The reaction mixture was filtered and concentrated in vacuo, and the residue partitioned between EtOAc (100 ml) and water (100 ml) which resulted in a formation of a white precipitate. Both layers were filtered through Celite and separated. The aqueous layer was extracted with EtOAc (2×100 ml), the combined organic layer was washed with brine (100 ml), dried (MgSO4), filtered and evaporated in vacuo to give the crude product, which was purified by flash chromatography (Biotage, 50 g) eluting with Pet Ether:EtOAc (75:25 to 50:50) to give the product (1.7 g) as a clear oil which solidified on standing to a beige solid.

1H NMR (500 MHz, Chloroform-d) δ 8.23 (d, J=5.4 Hz, 1H), 7.52 (ddd, J=7.6, 2.3, 1.1 Hz, 1H), 6.99 (dd, J=7.3, 5.3 Hz, 1H), 5.27 (s, 2H), 3.70 (dd, J=9.0, 7.5 Hz, 2H), 3.60 (s, 2H), 1.04-0.92 (m, 2H), −0.01 (s, 9H).

LCMS clean product at Rt=3.99 min (7 min method) m/z 264.9 [MH]+

Preparatory Example 9

1'-(2-trimethylsilylethoxymethyl)-spiro[cyclopropane-1,3'-pyrrolo[2,3-b]pyridine]-2'-one To a solution of 1-(2-trimethylsilylethoxymethyl)-3H-pyrrolo[2,3-b]pyridin-2-one (1.22 g, 4.61 mmol) in N,N-dimethylformamide (15 mL) at 0° C. was added sodium hydride 60% dispersion in mineral oil (461.42 mg, 11.54 mmol) and the reaction was stirred at 0° C. for 30 min. Next 1,2-dibromoethane (0.42 mL, 4.84 mmol) was added and the reaction mixture was allowed to warm up slowly to room temperature overnight. LCMS showed reaction incomplete—SM:product ratio ~1:2, with the expected product present at Rt=4.62 min (7 min method) m/z 290.9 [MH]+.

The reaction was quenched with water (50 ml), extracted into EtOAc (100 ml), the organic layer was washed with brine (3×50 ml), dried (MgSO4), filtered and evaporated in vacuo to give the crude product as an orange oil, which was purified by flash chromatography (50 g) eluting with pet ether:EtOAC (75:25 to 50:50) to give the product (679 mg) as a clear oil and the recovered starting material (231 mg).

1H NMR (500 MHz, Chloroform-d) δ 8.21 (d, J=5.3 Hz, 1H), 7.11 (d, J=7.2 Hz, 1H), 6.96 (dd, J=7.3, 5.2 Hz, 1H), 5.34 (s, 2H), 3.72 (dd, J=9.0, 7.5 Hz, 2H), 1.85 (q, J=4.2 Hz, 2H), 1.58 (q, J=4.2 Hz, 2H), 1.06-0.94 (m, 2H), −0.01 (s, 9H).

LCMS—product at Rt=4.72 min m/z 290.9 [MH]+

Preparatory Example 10

Spiro(1H-pyrrolo[2,3-b]pyridine-3,1'-cyclopropane)-2-one

To a solution of 1'-(2-trimethylsilylethoxymethyl)spiro(cyclopropane-1,3'-pyrrolo[2,3-b]pyridine)-2'-one (210. mg, 0.72 mmol) in dichloromethane (2 mL) was added 2,2,2-trifluoroacetic acid (1.9 mL, 24.81 mmol) and the reaction mixture was stirred at room temperature for 16 hours. LCMS showed the intermediate is present where SEM group had been cleaved to RCH2OH at Rt=0.67 min (7 min method) m/z 190.9 [MH]+. The volatiles were removed in vacuo, the residue was dissolved in dichloromethane (2 mL) and treated with ethylenediamine (0.19 mL, 2.89 mmol) and the reaction mixture was stirred at room temperature overnight. LCMS showed the reaction complete with the expected product present at Rt=0.88 min (100-500 MW, 7 min method) m/z 161 [MH]+. The reaction mixture was diluted with sat aqueous NaHCO3 and extracted into dichloromethane (5×50 ml), the organics were dried (MgSO4), filtered and concentrated to dryness under reduced pressure to give the crude product as a white solid which was purified by flash chromatography (Biotage, 10 g) eluting with DCM:MeOH (100:0 to 95:5) to give the final product as a white solid (102 mg).

1H NMR (500 MHz, Chloroform-d) δ 8.15 (dd, J=5.1, 1.6 Hz, 1H), 7.13 (dd, J=7.1, 1.6 Hz, 1H), 6.96 (dd, J=7.3, 5.2 Hz, 1H), 1.85 (q, J=4.3 Hz, 2H), 1.59 (q, J=4.3 Hz, 2H).

Preparatory Example 11 tert-butyl N-[[2-[(2'-oxo-spiro[cyclopropane-1,3'-pyrrolo[2,3-b]pyridine]-1'-yl)methyl]-1-(4,4,4-trifluorobutyl)benzimidazol-5-yl]methyl]carbamate To a solution of spiro[1H-pyrrolo[2,3-b]pyridine-3,1'-cyclopropane]-2-one (Preparatory example 10, 98. mg, 0.6100 mmol) in N,N-dimethylformamide (2.5 mL) at 0° C. was added sodium hydride (60% dispersion in mineral oil) (36.71 mg, 0.92 mmol) and the reaction mixture was stirred for 30 min. Next was added tert-butyl N-[[2-(chloromethyl)-1-(4,4,4-trifluorobutyl)benzimidazol-5-yl]methyl]carbamate (Preparatory Example 5, 248.31 mg, 0.6100 mmol) and the reaction was allowed to warm up to room temperature over weekend (for convenience). LCMS showed the reaction is essentially complete with the expected intermediate present at Rt=3.20 min (7 min method) m/z 530 [MH]+.

The reaction was quenched with water, diluted with EtOAc (50 ml) and the organics were washed with brine (3×50 ml), dried with MgSO$_4$, filtered and evaporated in vacuo. The residue was purified by column chromatography (Biotage, 10 g) eluting with DCM:MeOH (100:0 to 95:5) to give the product (187 mg) as a yellow oil.

1H NMR (500 MHz, DMSO-d6) δ 8.02 (dd, J=5.1, 1.6 Hz, 1H), 7.53 (d, J=8.4 Hz, 1H), 7.47 (dd, J=7.3, 1.6 Hz, 1H), 7.32 (d, J=9.9 Hz, 2H), 7.12 (d, J=8.3 Hz, 1H), 7.01 (dd, J=7.3, 5.3 Hz, 1H), 5.26 (s, 2H), 4.43 (t, J=7.4 Hz, 2H), 4.16 (d, J=6.1 Hz, 2H), 2.42-2.35 (m, 3H), 2.01 (q, J=7.8 Hz, 2H), 1.78 (q, J=4.0, 3.5 Hz, 2H), 1.66 (q, J=3.8 Hz, 2H), 1.36 (s, 9H).

LCMS product at Rt=3.38 min (7 min method) m/z 530 [MH]+

Preparatory Example 12 tert-butyl N-[[1-isopentyl-2-[(2'-oxo-spiro[cyclopropane-1,3'-pyrrolo[2,3-b]pyridine]-1'-yl)methyl]benzimidazol-5-yl]methyl]carbamate To spiro[1H-pyrrolo[2,3-b]pyridine-3,1'-cyclopropane]-2-one (Preparatory Example 10, 90. mg, 0.5600 mmol) in N,N-dimethylformamide (2 mL) to 0° C. was added sodium hydride (60% dispersion in mineral oil) (29.22 mg, 0.7300 mmol) and the reaction mixture was stirred at that temperature for 1 hour. tert-butyl N-[[2-(chloromethyl)-1-isopentyl-benzimidazol-5-yl]methyl]carbamate (obtained according to the procedure set out in WO 2010/103306, 205.6 mg, 0.5600 mmol) was added and the reaction mixture was slowly allowed to warm up to room temperature overnight. LCMS shows the expected product is present (Rt=3.24 min m/z 490), plus unreacted RHS (Rt=0.88 min m/z 161) and an impurity (Rt=2.37 min m/z 508).

The reaction mixture was quenched with water (1 ml), diluted with EtOAc (100 ml), and washed with brine (3×50 ml), the organic layer was dried (MgSO$_4$), filtered and evaporated in vacuo. The crude was purified by column purification (Biotage, 10 g) eluting with MeOH:DCM (gradient 0:100 to 5:95) to give a light yellow oil, with was azeotroped with Petroleum Ether to give the final product as a cream-coloured foam, dried to a constant weight under vacuum (115 mg).

1H NMR (500 MHz, Chloroform-d) δ 8.15 (d, J=5.4 Hz, 1H), 7.85 (s, 1H), 7.36 (s, 2H), 7.12 (dd, J=7.4, 1.5 Hz, 1H), 6.95 (dd, J=7.4, 5.3 Hz, 1H), 5.53 (s, 2H), 4.93 (s, 1H), 4.43 (d, J=5.8 Hz, 2H), 4.33 (t, J=8.1 Hz, 2H), 1.90 (q, J=4.3 Hz, 2H), 1.63 (dq, J=10.1, 5.9, 4.9 Hz, 5H), 1.46 (s, 9H)

LCMS—clean product at Rt=3.15 min m/z 490 [MH]+.

Preparatory Example 13

Spiro[1H-pyrrolo[2,3-c]pyridine-3,1'-cyclopropane]-2-one

To a red suspension of 1,3-dihydropyrrolo[2,3-c]pyridin-2-one hydrochloride (767. mg, 4.49 mmol) and diisopropylamine (2.52 mL, 17.98 mmol) in tetrahydrofuran (40 mL) under N$_2$ was cooled down at −40° C. using a dry ice/acetonitrile bath. n-Butyllithium solution (9.5 mL, 23.75 mmol) was added drop wise over 60 min, via syringe. When addition was complete, the dry ice/acetonitrile bath was changed for an ice bath and when the reaction temperature reached 0° C., a solution of 1,2-dibromoethane (0.77 mL, 9.0 mmol) in THF (5 ml) was added dropwise over 90 min, and a further addition of THF (15 ml) led to a red suspension. The reaction mixture was allowed to warm slowly to rt (without removing the ice bath) and it was left stirring at room temperature from 18:30 overnight. Carefully addition of saturated aqueous NH$_4$Cl solution (60 ml) and phases were separated. The dark red viscous aqueous phase was extracted with EtOAc (5×60 ml). Organics were combined, washed with brine (1×50 ml) dried using MgSO$_4$, filtered through a sinter and concentrated under vacuum. The resulting crude beige solid material (250 mg) was adsorbed onto silica and chromatographed using a 10 g pre-packed Biotage cartridge, gradient elution with a mixture of DCM 90% and DCM/MeOH/NH$_3$ (9:1:0.2) 10% with further gradients of this mixture up to 100%. Fractions containing product were collected, combined and concentrated under vacuum to afford 77 mg of the product as a yellow-brown solid.

LCMS-LCQ: M/Z [M+H]+: 161.27 RT: 0.45 min

1H-NMR: 1H NMR (500 MHz, DMSO-d6) δ 10.70 (s, 1H), 8.33-8.02 (m, 2H), 7.06 (d, J=4.7 Hz, 1H), 1.70 (q, J=3.8, 3.4 Hz, 2H), 1.57 (q, J=3.8 Hz, 2H).

Preparatory Example 14 tert-butyl N-[[1-isopentyl-2-[(2'-oxospiro[cyclopropane-1,3'-pyrrolo[2,3'-c]pyridine]-1'-yl)methyl]benzimidazol-5-yl]methyl]carbamate To a solution of spiro[1H-pyrrolo[2,3-c]pyridine-3,1'-cyclopropane]-2-one (Preparatory Example 13, 77.04 mg, 0.4800 mmol) in N,N-dimethylformamide (2 mL) cooled to 0° C. using an ice bath, sodium hydride (60% dispersion in mineral oil) (22.74 mg, 0.5700 mmol) was added in one portion and the reaction mixture was stirred at 0° C. for 1 hour. A solution of tert-butyl N-[[2-(chloromethyl)-1-isopentyl-benzimidazol-5-yl]methyl]carbamate (160. mg, 0.4400 mmol) tert-butyl N-[[2-(chloromethyl)-1-isopentyl-benzimidazol-5-yl]methyl]carbamate (160. mg, 0.4400 mmol)□ in DMF (1 ml) was slowly added dropwise for 1 h and the reaction mixture was left stirring at room temperature overnight. H$_2$O (3 ml) was added and crude material was concentrated in vacuo using n-heptane (4×12 ml) to remove as much DMF as possible. Addition of H$_2$O (60 ml) and crude was extracted using EtOAc (5×20 ml). Organics were separated, combined, washed with brine (1×50 ml), dried using MgSO$_4$, filtered though a sinter and concentrated under vacuum to afford crude material which was triturated with ether (2×7 ml). The resulting solid adsorbed on silica and purified by flash chromatography, using a 10 g pre-packed Biotage column and gradient elution from DCM 100% to a mixture with DCM/MeOH/NH$_3$ (9:1:0.2) from 0% to 60%. The resulting solid on concentration of fractions was purified using a 5 g Grace column, with gradient elution from 100% EtOAc and an increasing gradient of a mixture EtOAc/MeOH (95:5) from 0% up to 100%. This gave the title compound as a white solid (62 mg).

LCMS-LCQ: M/Z [M+H]+: 490.08 RT: 2.57 min

1H NMR (500 MHz, Chloroform-d) δ 8.73 (s, 1H), 8.31 (d, J=19.9 Hz, 1H), 7.68 (s, 1H), 6.80 (s, 1H), 5.34 (s, 2H), 4.89 (s, 1H), 4.44 (s, 2H), 4.23 (dd, J=20.0, 12.8 Hz, 2H), 2.24-1.85 (m, 3H), 1.69 (s, 4H), 1.48 (s, 12H), 1.38-1.13 (m, 12H), 0.97 (d, J=6.2 Hz, 7H).

Preparatory Example 15

2-(Chloromethyl)-1-tetrahydropyran-4-yl-benzimidazole-5-carbonitrile

A mixture of 2-chloro-1,1,1-triethoxy-ethane (2.17 mL, 12.66 mmol)☐ and 3-amino-4-(tetrahydropyran-4-ylamino) benzonitrile (275. mg, 1.27 mmol)☐ was heated to 80° C. for 1 h. LCMS shows product and an intermediate. Excess reagent was removed under vacuum and the crude was purified by column chromatography (SiO$_2$ 10 g, eluent: 20% EtOAc in Petroleum Ether to 100% EtOAc. The second fraction collected was the desired product as a beige solid (100 mg)

LCMS-LCQ Rt: 2.08 m/z: 276 [M+H]

$^1$H NMR (500 MHz, DMSO-d6) δ 7.37-7.31 (m, 1H), 6.95 (s, 1H), 6.79 (d, J=8.3 Hz, 1H), 5.04 (d, J=8.2 Hz, 1H), 4.36-4.29 (m, 2H), 4.08 (s, 2H), 3.89-3.82 (m, 2H), 3.61 (d, J=11.2 Hz, 1H), 3.42 (t, J=11.7 Hz, 2H), 1.83 (d, J=12.0 Hz, 2H), 1.57-1.44 (m, 2H), 1.36-1.27 (m, 3H).

The first fraction collected was the intermediate as a white solid (230 mg) which was suspended in EtOH (3 ml) and heated for 4 h. The solvent was then evaporated to leave a brown solid, which was triturated with Et$_2$O and the solid filtered to give a further quantity of the desired product (87 mg)

$^1$H NMR (500 MHz, DMSO-d6) δ 8.22 (d, J=1.6 Hz, 1H), 7.96 (d, J=8.5 Hz, 1H), 7.65 (dd, J=8.5, 1.6 Hz, 1H), 5.19 (s, 3H), 4.79 (tt, J=12.5, 4.6 Hz, 2H), 4.05 (dd, J=11.6, 4.5 Hz, 3H), 3.55 (td, J=11.7, 2.1 Hz, 3H), 2.46-2.31 (m, 4H), 1.94-1.82 (m, 3H).

LCMS-LCQ Rt: 1.94 m/z: 276 [M+H]

Preparatory Example 16

2-[(6'-fluoro-2'-oxo-spiro[cyclopropane-1,3'-indoline]-1'-yl)methyl]-1-tetrahydropyran-4-yl-benzimidazole-5-carbonitrile A mixture of 6'-fluoro[spirocyclopropane-1,3'-indoline]-2'-one (Preparatory example 3, 128.5 mg, 0.7300 mmol) and 2-(chloromethyl)-1-tetrahydropyran-4-yl-benzimidazole-5-carbonitrile (Preparatory Example 15, 200. mg, 0.7300 mmol) and caesium carbonate (354.5 mg, 1.09 mmol) in acetonitrile (10 mL) was stirred at r.t. overnight. Volatiles were removed in vacuo, the residue was stirred in water (20 ml) and the suspension filtered to leave a grey solid, which was then triturated with Et$_2$O and the solid filtered (228 mg)
LCMS-MDAP Rt: 19.0 m/z: 417 [M+H]

$^1$H NMR (500 MHz, DMSO-d6) δ 8.18 (s, 1H), 7.90 (d, J=8.5 Hz, 1H), 7.59 (d, J=8.5 Hz, 1H), 7.12-7.02 (m, 2H), 6.80 (t, J=8.7 Hz, 1H), 5.43 (s, 2H), 4.84 (t, J=12.6 Hz, 1H), 4.03 (dd, J=12.3, 4.3 Hz, 2H), 3.51-3.44 (m, 2H), 2.43-2.33 (m, 2H), 1.82-1.73 (m, 2H), 1.69 (d, J=4.3 Hz, 2H), 1.57 (q, J=4.3, 3.7 Hz, 2H).

Preparatory Example 17

N-(4-chloro-2-nitro-phenyl)tetrahydropyran-4-amine

A mixture of 5-Chloro-2-fluoronitrobenzene (3.5 g, 19.94 mmol), tetrahydropyran-4-amine (2.29 ml, 21.93 mmol) and potassium carbonate (5.51 g, 39.88 mmol) in MeCN (100 mL) was stirred at 25° C. over weekend then heated to 50° C. until LCMS shows reaction complete. The reaction mixture was filtered and washed with EtOAc and concentrated to dryness to leave an orange solid (5.1 g)

1H NMR (500 MHz, Chloroform-d) δ 8.20 (d, J=2.6 Hz, 1H), 8.06 (d, J=7.3 Hz, 1H), 7.38 (dd, J=9.2, 2.6 Hz, 1H), 6.85 (d, J=9.2 Hz, 1H), 4.03 (dt, J=12.1, 3.8 Hz, 2H), 3.77-3.67 (m, 1H), 3.63-3.53 (m, 2H), 2.12-2.03 (m, 2H), 1.68 (dtd, J=14.1, 10.2, 4.1 Hz, 2H).

LCMS Rt: 4.31 m/z: 257 [M+H]

Preparatory Example 18

4-chloro-N1-tetrahydropyran-4-yl-benzene-1,2-diamine

An solution of potassium carbonate (16.48 g, 119.21 mmol) and sodium dithionite (27.67 g, 158.95 mmol) in water (30 mL) was added dropwise to a solution of N-(4-chloro-2-nitro-phenyl)tetrahydropyran-4-amine (5.1 g, 19.87 mmol) in acetonitrile (70 ml) and water (30 ml) and the reaction mixture was stirred at rt for about 48 h. LCMSRt: 1.97 m/z: 227 [M+H]

EtOAc (100 ml) was added to the reaction, the layers were separated and the aqueous layer further extracted with EtOAc (2×50 ml). The combined organic layer were washed with saturated brine solution (1×60 mL). The organics were dried (MgSO$_4$) and concentrated to dryness under reduced pressure lo leave a brown solid (4 g) and the crude was purified by column chromatography (SiO2 25 g, eluent 50% EtOAc in PE to 100% EtOAc) to give the title compound (2.0 g).

1H NMR (500 MHz, DMSO-d6) δ 6.54 (d, J=2.2 Hz, 1H), 6.49-6.38 (m, 2H), 4.83 (s, 2H), 4.29 (d, J=7.6 Hz, 1H), 3.86 (dt, J=11.6, 3.3 Hz, 2H), 3.39 (td, J=11.3, 2.2 Hz, 3H), 1.92-1.83 (m, 2H), 1.37 (qd, J=11.3, 4.2 Hz, 2H). LCMS-LCQ Rt: 1.79 m/z: 227 [M+H]

Preparatory Example 19

5-chloro-2-(chloromethyl)-1-tetrahydropyran-4-yl-benzimidazole

A mixture of 4-chloro-N1-tetrahydropyran-4-yl-benzene-1,2-diamine (1. g, 4.41 mmol) and 2-chloroacetic acid (0.63 g, 6.62 mmol) in 4M HCl (50 mL) was heated to 60° C. until LCMS showed completion (72 h). The reaction mixture was allowed to cool to r.t and the precipitate that formed was collected by filtration and was washed with H$_2$O (2×50 ml). The white residue was treated with a sat. solution of NaHCO$_3$ and the product extracted with EtOAc (3×100 ml) (slightly insoluble), dried (MgSO$_4$) and solvent evaporated to leave a light brown solid (658 mg, N2006-173-1)

1H NMR (500 MHz, DMSO-d6) δ 7.78 (d, J=8.8 Hz, 1H), 7.71 (d, J=2.1 Hz, 1H), 7.29 (dd, J=8.8, 2.1 Hz, 1H), 5.15 (s, 2H), 4.74 (tt, J=12.2, 4.4 Hz, 1H), 4.05 (dd, J=11.5, 4.5 Hz, 2H), 3.54 (td, J=11.9, 2.0 Hz, 2H), 2.45-2.34 (m, 2H), 1.88-1.80 (m, 2H).

LCMS-LCQ Rt: 3.24 m/z: 285 [M+]

Preparatory Example 20

4-(((1R,4R)-4-Hydroxycyclohexyl)amino)-3-nitrobenzonitrile

In a flask equipped with a reflux condenser, trans-4-aminocyclohexanol hydrochloride (2.70 g, 17.80 mmoles) was suspended in iso-propanol (15 ml). To this stirred suspension, triethylamine (4.40 ml, 31.49 mmoles) was slowly added, followed by 4-chloro-3-nitrobenzonitrile (2.50 g, 13.69 mmoles). The resulting yellow suspension was heated at 65° C. for 36 h, allowed to cool down to room temperature before water (10 ml) was added to the reaction mixture. The resulting precipitate was collected by filtration and successively washed with water and iso-propanol, to yield 4-(((1R,4R)-4-hydroxycyclohexyl)amino)-3-nitrobenzonitrile as a yellow crystalline solid (3.28 g, 12.55 mmoles, 92%). The resulting solid was further purified by recrystallization from hot ethanol.

m/z 262.2 [MH]+

$^1$H NMR (500 MHz, DMSO-d$_6$) δ 8.49 (s, 1H), 8.18 (d, J=7.8 Hz, 1H), 7.79 (d, J=9.0 Hz, 1H), 7.26 (d, J=9.1 Hz, 1H), 4.63 (s, 1H), 3.67 (dtd, J=14.9, 10.4, 4.0 Hz, 1H), 3.57-3.41 (m, 1H), 2.05-1.88 (m, 2H), 1.89-1.75 (m, 2H), 1.53-1.19 (m, 4H).

Preparatory Example 21

3-Amino-4-(((1R,4R)-4-hydroxycyclohexyl)amino)benzonitrile

A flask flushed with nitrogen was successively charged with 4-(((1R,4R)-4-hydroxycyclohexyl)amino)-3-nitrobenzonitrile from Preparatory Example 20 (1.31 g, 5.01 mmoles), 10% palladium on carbon (0.131 g) and methanol (40 ml). The flask was then flushed with hydrogen and the reaction mixture left to stir under a hydrogen atmosphere (hydrogen balloon). After 3 h, Pd/C 10% was removed by filtration and the filtrate concentrated in vacuo. Chromatography on silica (dichloromethane/ethanol/ammonia, 200/8/1) provided 3-amino-4-(((1R,4R)-4-hydroxycyclohexyl)amino)benzonitrile as an off-white crystalline solid (0.253 g, 1.09 mmoles, 22%).

m/z 232.2 [MH]+

$^1$H NMR (500 MHz, DMSO-d$_6$) δ 6.89 (dd, J=8.2, 2.0 Hz, 1H), 6.75 (d, J=2.0 Hz, 1H), 6.49 (d, J=8.2 Hz, 1H), 5.02 (d, J=7.4 Hz, 1H), 4.94 (s, 2H), 4.57 (d, J=4.3 Hz, 1H), 3.44 (d, J=11.8 Hz, 2H), 3.24 (ddd, J=10.6, 7.2, 3.7 Hz, 1H), 1.94 (dd, J=11.8, 4.1 Hz, 3H), 1.89-1.79 (m, 3H), 1.35-1.19 (m, 5H).

Preparatory Example 22

2-(Chloromethyl)-1-((1R,4R)-4-hydroxycyclohexyl)-1H-benzo[d]imidazole-5-carbonitrile In a flask equipped with a reflux condenser, 2-chloro-1,1,1-triethoxyethane (544 µl, 2.85 mmoles) was added at once to a solution of 3-amino-4-(((1R,4R)-4-hydroxycyclohexyl)amino)benzonitrile from Preparatory Example 21 (0.220 g, 0.95 mmoles) in ethanol (10 ml). The resulting solution was heated at 70° C. for 24 h, before more 2-chloro-1,1,1-triethoxyethane (544 µl, 2.85 mmoles) was added and heating continued for a further 24 h. The resulting solution was allowed to cool down to room temperature and the solvent removed in vacuo. Chromatography on silica (dichloromethane/ethanol/ammonia, 200/8/1) provided 2-(chloromethyl)-1-((1R,4R)-4-hydroxycyclohexyl)-1H-benzo[d]imidazole-5-carbonitrile as a white crystalline solid (0.251 g, 0.86 mmoles, 91%).

m/z 289.9 [MH]+

$^1$H NMR (500 MHz, DMSO-d6) δ 8.20-8.14 (m, 1H), 8.01 (dd, J=8.6, 2.0 Hz, 1H), 7.65-7.57 (m, 1H), 5.16 (d, J=1.9 Hz, 2H), 4.74 (s, 1H), 4.47 (tt, J=12.5, 4.1 Hz, 1H), 3.71 (tt, J=10.4, 4.3 Hz, 1H), 2.26 (ddt, J=16.3, 12.4, 6.2 Hz, 2H), 2.05-1.93 (m, 2H), 1.92-1.82 (m, 2H), 1.51-1.38 (m, 2H).

Preparatory Example 23

2-((6'-Fluoro-2'-oxospiro[cyclopropane-1,3'-indolin]-1'-yl)methyl)-1-((1R,4R)-4-hydroxycyclohexyl)-1H-benzo[d]imidazole-5-carbonitrile To a solution of 6'-fluorospiro[cyclopropane-1,3'-indolin]-2'-one from Preparatory Example 4 (0.084 g, 0.475 mmoles) in acetonitrile (5 ml) was successively added 1,8-diazabicyclo[5.4.0]undec-7-ene (142 µl, 0.95 mmoles) and 2-(chloromethyl)-1-((1'R,4'R)-4'-hydroxycyclohexyl)-1H-benzo[d]imidazole-5-carbonitrile from Preparatory Example 22 (0.165 g, 0.57 mmoles). The resulting suspension was heated at 90° C. for 2 h. The resulting deep purple solution was allowed to cool down to room temperature before water (20 ml) was added. The resulting precipitate was collected by filtration, washed with water and purified by chromatography on silica (100% ethyl acetate), yielding 2-((6'-fluoro-2'-oxospiro[cyclopropane-1,3'-indolin]-1'-yl)methyl)-1-((1R,4R)-4-hydroxycyclohexyl)-1H-benzo[d]imidazole-5-carbonitrile as a white crystalline solid (0.165 g, 0.38 mmoles, 67%).

m/z 431.0 [MH]+

$^1$H NMR (500 MHz, DMSO-d$_6$) δ 8.17 (d, J=1.7 Hz, 1H), 7.95 (d, J=8.6 Hz, 1H), 7.56 (dd, J=8.6, 1.6 Hz, 1H), 7.09-7.01 (m, 2H), 6.79 (ddd, J=10.3, 8.3, 2.4 Hz, 1H), 5.38 (s, 2H), 4.72 (d, J=4.4 Hz, 1H), 4.51 (s, 1H), 3.72-3.60 (m, 1H), 2.27-2.16 (m, 2H), 1.92 (d, J=12.2 Hz, 2H), 1.70 (dt, J=6.9, 4.2 Hz, 4H), 1.58 (q, J=3.8 Hz, 2H), 1.42-1.29 (m, 2H).

Example 1

1'-{[5-(Aminomethyl)-1-(4,4,4-trifluorobutyl)-1H-1,3-benzodiazol-2-yl]methyl}-6'-fluoro-1',2'-dihydrospiro[cyclopropane-1,3'-indole]-2'-one To a solution of tert-butyl N-[(2-[(6'-fluoro-2'-oxo-1',2'-dihydro[spirocyclopropane-1,3'-indole]-1'-ylmethyl]-1-(4,4,4-trifluorobutyl)-1H-1,3-benzodiazyl)methyl]carbamate from Preparatory Example 6 (1030 mg, 1.88 mmol) in dichloromethane (3.5 mL) under nitrogen was added hydrogen chloride solution (2M in Et$_2$O) (12.54 mL, 25.08 mmol). A pink/white solid precipitate formed almost immediately and the heterogenous mixture was stirred at room temperature for 6 hours. The reaction mixture was then concentrated under vacuum at room temperature and azeotroped further with 3×20 ml DCM. The crude product was sonicated and triturated with diethyl ether (2×15 ml then 3×10 ml). The solvent was removed by decantation and triturated further with 10 ml ether. The mixture was filtered and dried to give 865 mg of the desired product as an off white solid as crude HCl salt. (95% crude yield).

The crude HCl salt was partitioned between ethyl acetate (80 ml) and saturated aqueous sodium bicarbonate (80 ml). The organics were separated and the aqueous was extracted with further ethyl acetate (3×30 ml). The organics were combined, dried over magnesium sulphate, filtered and concentrated under vacuum. The residue was purified using flash chromatography, (25 g pre-packed Biotage cartridge, silica adsorbed material and eluted with Dichloromethane/ethanol/ammonia (100:0:0 gradient to 95:5:1) to afford 539 mg (65% yield) of the desired product free base as a white solid.
LCMS:
M/Z [M+H]+: 447.10
1H-NMR:
1H NMR (500 MHz, DMSOd6) δ 7.56 (s, 1H), 7.51 (d, J=8.3 Hz, 1H), 7.23 (d, J=8.3 Hz, 1H), 7.19-7.12 (m, 1H), 7.06 (dd, J=8.3, 5.3 Hz, 1H), 6.85-6.76 (m, 1H), 5.28 (s, 2H), 4.35 (t, J=7.5 Hz, 2H), 3.77 (s, 2H), 2.32 (dt, J=21.6, 8.1 Hz, 2H), 1.83 (p, J=8.1 Hz, 2H), 1.67 (q, J=3.9, 3.4 Hz, 2H), 1.57 (q, J=4.2, 3.7 Hz, 2H).

Example 2

1'-{[5-(Aminomethyl)-1-(4,4,4-trifluorobutyl)-1H-1,3-benzodiazol-2-yl]methyl}-6'fluoro-1',2'-dihydrospiro[cyclopropane-1,3'-indole]-2'-one, Hydrochloride To a solution of 1'-{[5-(aminomethyl)-1-(4,4,4-trifluorobutyl)-1H-1,3-benzodiazol-2-yl]methyl}-6'fluoro-1',2'-dihydrospiro[cyclopropane-1,3'-indole]-2'-one from Example 1 (539. mg, 1.21 mmol) in dichloromethane (10 mL) was added hydrogen chloride solution 2.0 M in diethyl ether (0.6 mL, 1.21 mmol) dropwise and the reaction mixture stirred for 30 min. The solvent was then evaporated under vacuum. The residue was dissolved in 20 ml MeOH and concentrated under vacuum at room temperature and dried further at 40° C. leading to product as a HCl salt.
LCMS:
M/Z [M+H]+: 447.05
1H-NMR:
1H NMR (500 MHz, DMSO-d6) δ 8.36 (s, 3H), 7.77 (s, 1H), 7.71 (d, J=8.3 Hz, 1H), 7.42 (d, J=8.2 Hz, 1H), 7.15 (dd, J=9.6, 2.4 Hz, 1H), 7.08 (dd, J=8.3, 5.4 Hz, 1H), 6.82 (ddd, J=10.5, 8.3, 2.4 Hz, 1H), 5.35 (s, 2H), 4.41 (t, J=7.7 Hz, 2H), 4.09 (q, J=5.8 Hz, 2H), 2.43-2.26 (m, 2H), 1.87 (p, J=8.0 Hz, 2H), 1.63 (dq, J=54.6, 4.2 Hz, 4H).

Example 3

1'-((5-(aminomethyl)-1-(4,4,4-trifluorobutyl)-1H-benzo[d]imidazol-2-yl)methyl)spiro[cyclopropane-1,3'-pyrrolo[2,3-b]pyridin]-2'(1'H)-one A suspension of tert-butyl N-[[2-[(2'-oxo[spirocyclopropane-1,3'-pyrrolo[2,3-b]pyridine]-1'-yl)methyl]-1-(4,4,4-trifluorobutyl)benzimidazol-5-yl]methyl]carbamate (Preparatory Example 11, 184. mg, 0.35 mmol) in dichloromethane (4 mL) was treated with trifluoroacetic acid (1.86 mL, 24.32 mmol) and the resulting solution was left stirring for 1 hr at room temperature. The volatiles were removed under reduced pressure, the residue was purified by SCX-2 cartridge, eluting first with MeOH and then with a 2M NH₃ solution in MeOH. Fractions containing product were combined, evaporated in vacuo and further purified by column chromatography (Biotage, 10 g) eluting with DCM:MeOH:NH₃ (98:2:0.2 to 90:10:1). ☐Fractions containing product were combined and solvent evaporated to give a white solid which was further dried under vacuum at 40 C in vacuum pistol to give the product (113 mg).
1H NMR (500 MHz, DMSO-d6) δ 8.06-7.98 (m, 1H), 7.51 (d, J=8.3 Hz, 1H), 7.47 (d, J=7.2 Hz, 1H), 7.43 (s, 1H), 7.19 (d, J=8.3 Hz, 1H), 7.00 (dd, J=7.3, 5.3 Hz, 1H), 5.26 (s, 2H), 4.43 (t, J=7.4 Hz, 2H), 3.74 (s, 2H), 2.44-2.33 (m, 2H), 2.00 (dd, J=15.1, 7.5 Hz, 2H), 1.78 (q, J=4.0, 3.5 Hz, 2H), 1.65 (q, J=4.2, 3.8 Hz, 2H). ☐
LCMS Rt: 0.51-0.69 min m/z: 430 [M+H]+

Example 4

1'-((5-chloro-1-(tetrahydro-2H-pyran-4-yl)-1H-benzo[d]imidazol-2-yl)methyl)spiro[cyclopropane-1,3'-pyrrolo[2,3-c]pyridin]-2'(1'H)-one To a solution of spiro[1H-pyrrolo[2,3-c]pyridine-3,1'-cyclopropane]-2-one (30. mg, 0.1900 mmol, Preparatory Example 13) in dimethylformamide (3 mL) at 0° C. was added 60% sodium hydride (8.99 mg, 0.2200 mmol) was stirred for 5 min at 0° C. and for another 10 at r.t. before adding a solution of 5-chloro-2-(chloromethyl)-1-tetrahydropyran-4-yl-benzimidazole (53.41 mg, 0.1900 mmol, Preparatory Example 19) in N,N-dimethylformamide (3 mL).
After 30 min LCMS shows no RHS left so the reaction mixture was quenched with H₂O (5 ml) and product extracted into EtOAc (3×30 ml). Combined organic layers were washed with brine, dried (MgSO4) and solvent evaporated to leave an orange oil. (82 mg) which was purified by column chromatography (SiO2 10 g, eluent:100% EtOAc to 5% MeOH in EtOAc) and the product re-chromatographed by column chromatography (6 g SiO₂; 100% EtOAc). Fractions containing product were combined and solvent evaporated and dried overnight in vacuum pistol at 40° C. A light yellow solid was obtained (16 mg, N2006-192-2)
1H NMR (500 MHz, DMSO-d6) δ 8.40 (s, 1H), 8.24 (d, J=4.8 Hz, 1H), 7.72 (d, J=9.9 Hz, 2H), 7.23 (d, J=8.8 Hz, 1H), 7.15 (d, J=4.6 Hz, 1H), 5.44 (s, 2H), 4.80 (dq, J=12.5, 6.8, 5.0 Hz, 1H), 4.02 (dd, J=11.1, 4.7 Hz, 3H), 3.45 (t, J=11.6 Hz, 2H), 2.35 (qd, J=12.3, 4.4 Hz, 3H), 1.84 (q, J=4.1, 3.7 Hz, 2H), 1.71 (dq, J=8.2, 4.2 Hz, 5H).
LCMS-MDAP Rt: 11.84 mz: 409 [M+H]

Example 5

1'-((5-(aminomethyl)-1-isopentyl-1H-benzo[d]imidazol-2-yl)methyl)[spirocyclopropane-1,3'-pyrrolo[2,3-b]pyridin]-2'(1'H)-one A suspension of tert-butyl N-[[1-isopentyl-2-[(2'-oxo[spirocyclopropane-1,3'-pyrrolo[2,3-b]pyridine]-1'-yl)methyl]benzimidazol-5-yl]methyl]carbamate (Preparatory Example 12, 115. mg, 0.2300 mmol) in dichloromethane (3 mL) was treated with trifluoroacetic acid (1.26 mL, 16.44 mmol) and the resulting solution was left stirring for 1 hr at room temperature. LCMS showed product present at Rt: 1.24 min m/z: 390 [MH]+. The volatiles were removed under reduced pressure, the residue was purified by SCX-2 cartridge, eluting first with MeOH and then with a 2M NH₃ solution in MeOH. Fractions containing product were combined, evaporated in vacuo and further purified by column chromatography (Biotage, 10 g) eluting with DCM:MeOH:NH₃

(98:2:0.2 to 90:10:1). Fractions containing product were combined and solvent evaporated to give a white solid which was further dried under vacuum at 40 C in vacuum pistol to give the product (60 mg).

1H NMR (500 MHz, DMSO-d6) δ 8.06 (d, J=5.3 Hz, 1H), 7.53-7.36 (m, 3H), 7.18 (d, J=8.1 Hz, 1H), 7.02 (t, J=6.5 Hz, 1H), 5.25 (s, 2H), 4.31 (t, J=7.6 Hz, 2H), 3.74 (s, 2H), 1.84-1.73 (m, 2H), 1.71-1.53 (m, 5H), 0.94 (d, J=5.8 Hz, 6H).

LCMS Rt: 0.51-0.69 min m/z: 390 [M+H]+□LCMS-MDAP: Rt=10.77 min m/z 390 [MH]+

Example 6

1'-((5-(aminomethyl)-1-isopentyl-1H-benzo[d]imidazol-2-yl)methyl)spiro[cyclopropane-1,3'-pyrrolo[2,3-c]pyridin]-2'(1'H)-one A suspension of tert-butyl N-[[1-isopentyl-2-[(2'-oxospiro[cyclopropane-1,3'-pyrrolo[2,3-c]pyridine]-1'-yl)methyl]benzimidazol-5-yl]methyl]carbamate (Preparatory Example 14, 62 mg, 0.1300 mmol) in dichloromethane (2 mL) was treated with trifluoro acetic acid (0.68 mL, 8.86 mmol) and the resulting solution was left stirring for 1 hr at room temperature. The volatiles were removed under reduced pressure, the residue was purified by SCX-2 cartridge, eluting first with MeOH and then with a 2M $NH_3$ solution in MeOH. Fractions containing product were combined, evaporated in vacuo and further purified by column chromatography (Biotage, 5 g) eluting with $DCM:MeOH:NH_3$ (98:2:0.2) from 0% up to 100% of this mixture. Fractions containing product were combined and solvent evaporated to give a white solid. Further ether trituration (3×6 ml) was performed to remove additional impurities to give slightly impure title compound (60 mg).

LCMS-LCQ: M/Z [M+H]+: 390.4 RT: 0.47 min□

1H NMR (500 MHz, DMSO-d6) δ 8.42 (s, 1H), 8.24 (d, J=4.9 Hz, 1H), 7.57 (s, 1H), 7.42 (d, J=8.4 Hz, 1H), 7.22 (d, J=8.4 Hz, 1H), 7.16 (d, J=4.8 Hz, 1H), 5.32 (s, 2H), 4.26 (t, J=8.2 Hz, 2H), 3.79 (s, 2H), 1.85 (q, J=4.0 Hz, 2H), 1.71 (q, J=4.3, 3.9 Hz, 2H), 1.68-1.58 (m, 1H), 1.46 (q, J=7.5 Hz, 2H), 0.92 (d, J=6.5 Hz, 7H).

Example 7

1'-((5-(aminomethyl)-1-(tetrahydro-2H-pyran-4-yl)-1H-benzo[d]imidazol-2-yl)methyl)-6'-fluorospiro[cyclopropane-1,3'-indolin]-2'-one 2-[(6'-fluoro-2'-oxo-spiro[cyclopropane-1,3'-indoline]-1'-yl)methyl]-1-tetrahydropyran-4-yl-benzimidazole-5-carbonitrile (Preparatory Example 16, 100 mg, 0.2400 mmol) was dissolved in a mixture of $THF/NH_3$ (6/0.5 ml) and hydrogenated by passing the solution through a small cartridge of Ni—Ra in the H-Cube at 1 ml/min at 20 bar and 45° C. for about 45 min. The solvent was evaporated to leave the title compound as a white solid (105 mg)

1H NMR (600 MHz, DMSO-d6) δ 7.59-7.54 (m, 2H), 7.16 (dd, J=8.5, 1.7 Hz, 1H), 7.10 (dd, J=9.7, 2.4 Hz, 1H), 7.03 (dd, J=8.2, 5.3 Hz, 1H), 6.78 (ddd, J=10.4, 8.3, 2.4 Hz, 1H), 5.34 (s, 2H), 4.73 (tt, J=12.2, 4.3 Hz, 1H), 4.00 (dd, J=11.5, 4.4 Hz, 2H), 3.74 (s, 2H), 3.41 (td, J=11.9, 1.9 Hz, 2H), 2.36 (qd, J=12.4, 4.6 Hz, 2H), 1.67 (q, J=3.9 Hz, 2H), 1.62 (dd, J=13.0, 3.9 Hz, 2H), 1.55 (q, J=3.8 Hz, 2H).

LCMS-MDAP Rt: 10.68 m/z: 421 [M+H]

Example 8

1'-((5-(Aminomethyl)-1-((1R,4R)-4-hydroxycyclohexyl)-1H-benzo[d]imidazol-2-yl)methyl)-6'-fluorospiro[cyclopropane-1,3'-indolin]-2'-one A flask flushed with nitrogen was successively charged with 2-((6'-fluoro-2'-oxospiro[cyclopropane-1,3'-indolin]-1'-yl)methyl)-1-((1R,4R)-4-hydroxycyclohexyl)-1H-benzo[d]imidazole-5-carbonitrile (0.139 g, 0.32 mmoles), 10% palladium on carbon (0.014 g), methanol (4 ml) and 37% hydrochloric acid (159 μl, 1.615 mmoles). The flask was flushed with hydrogen and stirred under a hydrogen atmosphere for 3 h. Water (10 ml) was added to the reaction mixture, the catalyst removed by filtration and the filtrate concentrated in vacuo. Partition of the residue between water (20 ml) and ethyl acetate (10 mL) was followed by extraction of the aqueous phase with ethyl acetate (2×10 ml). The aqueous layer was taken to pH=10 using a 30% aqueous ammonia solution and the resulting suspension extracted with ethyl acetate (4×20 ml). The combined organic extracts were washed with brine (50 ml), dried over sodium sulfate and concentrated in vacuo, yielding 1'-((5-(aminomethyl)-1-((1R,4R)-4-hydroxycyclohexyl)-1H-benzo[d]imidazol-2-yl)methyl)-6'-fluorospiro[cyclopropane-1,3'-indolin]-2'-one as a white solid (0.117 g, 0.27 mmoles, 84%). The resulting solid was further purified by recrystallization from hot ethanol.

m/z 435.2 [MH]+

1H NMR (600 MHz, DMSO-$d_6$) δ 7.59 (d, J=8.3 Hz, 1H), 7.56 (s, 1H), 7.12 (dd, J=8.5, 1.6 Hz, 1H), 7.07 (dd, J=9.6, 2.4 Hz, 1H), 7.03 (dd, J=8.2, 5.3 Hz, 1H), 6.77 (ddd, J=10.4, 8.2, 2.4 Hz, 1H), 5.29 (s, 2H), 4.65 (d, J=4.5 Hz, 1H), 4.41 (tt, J=12.3, 4.0 Hz, 1H), 3.74 (s, 2H), 3.61 (dp, J=15.6, 5.3, 4.6 Hz, 1H), 2.19 (qd, J=12.6, 3.3 Hz, 2H), 1.92-1.84 (m, 2H), 1.68 (q, J=3.8 Hz, 2H), 1.56 (dt, J=8.4, 3.8 Hz, 4H), 1.36-1.26 (m, 2H).

Example 9: In Vitro Efficacy

Compounds were subjected to RSV fusion assays and plaque reduction assays according to the following protocols.

RSV Fusion Assay

HEK 293T/17 cells were cultured in T75 culture flasks in Dulbecco's medium containing 10% FBS and 1× Penicillin-Streptomycin and warmed to 37° C. prior to use. The cells were passaged by first washing briefly with 3 ml PBS followed by a 4 min incubation with 3 TrypLE at 37° C. 7 ml media was then added to the flask and the cells dispersed via pipetting (×3) against the bottom of the flask. Two further T75 flasks were each seeded with $2×10^6$ cells in 15 ml fresh media.

Cells were seeded on the T75 plates at the same density as on the 6-well plates to the area of a T75 flask and one 1.75 cm radius well from a 6-well plate were compared. 7.79×2 ml of $3×10^5$ cells $ml^{-1}$ was used to seed a single T75 flask.

HEK cells were removed from a T75 flask as described above. The cells were counted and diluted to $3×10^5$ cells/ml in fresh media. Two T75 flasks were each seeded with 15.58 ml diluted cells.

The plasmid DNA (for pFR-Luc and pcDNA3.1_Gal4/NFκB) to be transfected into the HEK cells was first prepared in serum free media (DMEM+Pen/Strep) containing the transfection reagent Fugene 6 (Promega). Transfections were set up as follows (Luc=pFR_Luc, Gal4=pcDNA3.1+_Gal4/NFκB, A2_F=pcDNA3.1+_A2_F)

Transfections

| 1 | Luc + A2_F_1 |
|---|---|
| 2 | Gal4 |

Serum free media was placed in a 1.5 ml eppendorf tube then the fugene 6 was added into the media. The tube was vortexed for 1 s before being incubated at RT for 5 min. The plasmid DNA was then added to the tube, vortexed for 1 s, then incubated at RT for 15 min The transfection reagents were then added to the appropriate T75 flask by tipping the flask on end and adding the reagents directly to the media already in the flask. The flask was then tipped on its back so the media could be mixed thoroughly whilst not disturbing the cells before placing the flask the right way up and incubating overnight at 37° C. and 5% $CO_2$.

Compounds were diluted (in a polypropylene round-bottomed 96 well plate 1:3 in a twelve point dilution curve to give top [final] of either 3.3 µM, 1 µM, 500 nM 200 nM or 100 nM. The Control compound was always run at a concentration of 100 nM. The cells were then counted and diluted to $4×10^5$ cells/ml in fresh media. 50 µl of transfection population were added to all wells of the assay plates. 100 µl diluted compound (2 rows per compound), standard curve (one row) and controls (100 nM RV (100% inhibition, four wells), DMSO (0% inhibition, eight wells)) were added to the appropriate wells. 50 µl of the diluted ($4×10^5$ cells/ml) population 2 cells when then added to all wells.

The plates were then incubated for 24 hr at 37° C. and 5% $CO_2$

Buffers were prepared for the luciferase assay (20 mM tricine, 10 mM MgSO4, 1 mM EDTA, 10 mM DTT) and lysis and stored at −20° C. (25 mM tris-phosphate, 8 mM $MgCl_2$, 1 mM DTT, 1% Triton X-100, 15% glycerol). Luciferin substrate was prepared from and stored at −80 C (100 mM Tris-HCl, 15.76 g/L, Coenzyme A, 10.36 g/L, 23.5 mM luciferin, 7.48 g/L, 26.6 mM ATP, 14.66 g/L Luminescence was measured at appropriate time points as follows:

(a) Luciferase

Media was discarded into Virkon and the plates washed with 100 ul PBS per well. 20 ul/well of lysis buffer is added to each well and incubated shaking for 5 min at RT. Luciferin was added to LAAB at a dilution of 1:50 to give a working luciferin buffer. Add 100 µl working luciferin buffer to each well and luminescence was measured immediately.

(b) Resazurin

Media was discarded into Virkon and 100 ul SFM+20 ul CellTitre-Blue solution was added to each well. The plates were incubated 37° C., 5% $CO_2$ for 2 hrs. Resorufin fluorescence was measured at 590 nm.

Plaque Reduction Assay:

Vero cells were seeded in 96-well plates in a volume of 100 µL of Optimem supplemented with 3% FCS at a concentration of 4×104 cells per well. After an overnight incubation at 37° C. in a humidified 5% $CO_2$ atmosphere, the monolayer of cells should be approximately 90% confluent. Antiviral compounds were titrated in pre-warmed Serum Free (SF) Optimem in a U-bottom 96 well plate. For compounds titration in a DMSO solution, titration in 100% DMSO was performed first and each concentration added individually to a 2× final concentration at 4% DMSO in SF media before mixing with virus (2% final DMSO with virus). Media was then removed from cells and replaced with PBS (100 µl/well). RSV stock was thawed and diluted in SF Optimem media to 4000 PFU/mLl. An equal volume of virus was added to compounds on the titration plate. PBS was removed from cells which were then inoculated with the virus/compound solution (50 µL/well). Cells were incubated for 2 h in a 37° C.+5% $CO_2$ humidified incubator to allow infection. Inoculum was removed and media (Optimem+1% FCS) added to cells (100 µl/well). Cells were subsequently incubated for 48 h at 37° C.+5% $CO_2$ in a humidified incubator.

Immunostaining Procedure:

Media was removed from cells and the monolayer washed with PBS. Cells were fixed with ice cold 80% Acetone in PBS (100 µl/well) for 20 mins at −20° C. Fixative was removed and cells are dried for 30 mins with plates inverted. Blocking solution (5% skim milk powder in PBS-T) was added to cells (150 µL/well) and plates were incubated for 30 mins at room temperature. Blocking solution was removed and plates washed once with PBS-T. Primary antibody in blocking solution was added to plates (50 µl/well) and incubated for 1 h at 37° C. Plates were then washed 3 times with PBS-T. Secondary antibody in blocking solution was added to plates (50 µL/well) and incubated for 1 h at 37° C. in the dark. Plates were washed as above and then dried for 10 mins. Plates were scanned on the Odyssey Imager (Li-Cor Biosciences) at a resolution of 42 µM, medium quality and level 5 intensity in the 800 nM channel.

Data Analysis:

Images obtained were saved and plaque numbers counted with the aid of computer imaging software. $EC_{50}$ values for compounds were derived from dose response curves [three variable log (inhibitor) vs response] obtained using Graphpad Prism software.

Results

TABLE 1

| | RSV Plaque Reduction assays | | | | | | | | |
|---|---|---|---|---|---|---|---|---|---|
| | RSV Fusion Assay (n = 4) | | A2 (PRNT1) (n = 4) | | RSV-A5 (6440) (n = 1) | | RSV-A5 (6470) (n = 1) | | RSV-BA (Brasil) (n = 1) | |
| Compound | $IC_{50}$ (nM) | $IC_{90}$ (nM) | $IC_{50}$ (nM) | $IC_{90}$ (nM) | $IC_{50}$ (nM) | $IC_{90}$ (nM) | $IC_{50}$ (nM) | $IC_{90}$ (nM) | $IC_{50}$ (nM) | $IC_{90}$ (nM) |
| Example 1 | 1.1 | 9.4 | 2.1 | 13.5 | 5.7 | 106 | 10.3 | 81 | 2.1 | 34.5 |
| Example 5 | | | 5.3 | | | | | | | |
| Example 6 | | | 2.3 | | | | | | | |
| Example 7 | | | 1.6 | | | | | | | |
| Example 8 | | | 4.8 | | | | | | | |

Example 10: In Vitro Pharmacokinetics

Compounds were subjected to the following assays to investigate liver microsomal stability, permeability, plasma protein binding and calculated partition/distribution coefficients.

Microsomal Incubation: Experimental Procedure

Pooled human liver microsomes (pooled male and female), pooled rat liver microsomes (male Sprague Dawley rats) and pooled dog liver microsomes (male Beagle dog) are purchased from a reputable commercial supplier and stored at −80° C. prior to use.

Microsomes (final protein concentration 0.5 mg/mL), 0.1 M phosphate buffer pH 7.4 and test compound (final substrate concentration 3 µM; final DMSO concentration 0.25%) are pre-incubated at 37° C. prior to the addition of NADPH (final concentration 1 mM) to initiate the reaction. The final incubation volume is 50 µL. A control incubation is included for each compound tested where 0.1 M phosphate buffer pH 7.4 is added instead of NADPH (minus NADPH). Two control compounds are included with each species. All incubations are performed singularly for each test compound.

Compounds are incubated for 0, 5, 15, 30 and 45 min. The control (minus NADPH) is incubated for 45 min only. The reactions are stopped by transferring 25 µL of incubate to 50 µL methanol at the appropriate time points. The termination plates are centrifuged at 2,500 rpm for 20 min at 4° C. to precipitate the protein. Following protein precipitation, the sample supernatants are combined in cassettes of up to 4 compounds, internal standard is added and samples analysed by LC-MS/MS. From a plot of ln peak area ratio (compound peak area/internal standard peak area) against time, the gradient of the line is determined. Subsequently, half-life and intrinsic clearance are calculated MDR1-MDCK Permeability: Experimental Procedure MDR1-MDCK cells obtained from the NIH (Rockville, Md., USA) are used between passage numbers 6-30. Cells are seeded onto Millipore Multiscreen Transwell plates at 3.4×105 cells/cm2. The cells are cultured in DMEM and media is changed on day 3. On day 4 the permeability study is performed. Cell culture and assay incubations are carried out at 37° C. in an atmosphere of 5% CO2 with a relative humidity of 95%. On the day of the assay, the monolayers are prepared by rinsing both basolateral and apical surfaces twice with Hanks Balanced Salt Solution (HBSS) at the desired pH warmed to 37° C. Cells are then incubated with HBSS at the desired pH in both apical and basolateral compartments for 40 min to stabilise physiological parameters.

The dosing solutions are prepared by diluting test compound with assay buffer to give a final test compound concentration of 10 µM (final DMSO concentration of 1% v/v). The fluorescent integrity marker lucifer yellow is also included in the dosing solution. Analytical standards are prepared from test compound DMSO dilutions and transferred to buffer, maintaining a 1% v/v DMSO concentration.

For assessment of A-B permeability, HBSS is removed from the apical compartment and replaced with test compound dosing solution. The apical compartment insert is then placed into a companion plate containing fresh buffer (containing 1% v/v DMSO). For assessment of B-A permeability, HBSS is removed from the companion plate and replaced with test compound dosing solution. Fresh buffer (containing 1% v/v DMSO) is added to the apical compartment insert, which is then placed into the companion plate.

At 60 min the apical compartment inserts and the companion plates are separated and apical and basolateral samples diluted for analysis.

Test compound permeability is assessed in duplicate. Compounds of known permeability characteristics are run as controls on each assay plate.

Test and control compounds are quantified by LC-MS/MS cassette analysis using an 8-point calibration with appropriate dilution of the samples. The starting concentration (C0) is determined from the dosing solution and the experimental recovery calculated from C0 and both apical and basolateral compartment concentrations.

The integrity of the monolayer throughout the experiment is checked by monitoring lucifer yellow permeation using fluorimetric analysis. Lucifer yellow permeation is high if monolayers have been damaged.

Protein Binding Determination: Experimental Procedure

Solutions of test compound (5 µM, 0.5% final DMSO concentration) are prepared in buffer (pH 7.4) and 100% species-specific plasma. The experiment is performed using equilibrium dialysis with the two compartments separated by a semi-permeable membrane. The buffer solution is added to one side of the membrane and the plasma solution to the other side. After equilibration, samples are taken from both sides of the membrane. Standards are prepared in plasma and buffer and are incubated at 37° C.

Test compound incubations are performed in duplicate. A control compound is included in each experiment.

The solutions for each batch of compounds are combined into two groups (protein-free and protein-containing), then cassette analysed by LC-MS/MS using two sets of calibration standards for protein-free (7 points) and protein-containing solutions (6 points).

Log D Determination: Experimental Procedure 0.1 M phosphate buffer pH 7.4 (saturated with octanol) is added to the vial containing 1 mg of solid test compound and the solution mixed and sonicated for approximately 15 min. The solution is transferred to tubes, centrifuged and the supernatant is drawn off the top, leaving any solid compound in the bottom. This supernatant is then syringe filtered through 0.2 µm filters to produce the initial solution.

Three vials are prepared containing different ratios of octanol and compound in phosphate buffer in order to cover a range of log D values. The vials are mixed to equilibrium, then centrifuged to ensure the two phases are fully separated before the octanol is removed and the buffer samples analysed.

The aqueous solutions from the corresponding vials are then combined in cassettes of four and analysed using generic LC-MS/MS conditions. The amount of compound in each vial is quantified against a 6 point standard curve which is produced by serially diluting the initial solution. The log D is then calculated from these concentrations.

Log P Determination

Log P values were calculated with software available from ChemAxon using the method described in Viswanadhan et al.; *J. Chem. Inf. Comput. Sci.* 1989; 29:163-172.

Results

TABLE 2

| Pharmacokinetic Property | Value |
| --- | --- |
| Liver Microsomal Stability ($T_{1/2}$/mins; human/rat/dog) | Example 1: 32/80/532 |
| | Example 5: 219/115/390 |
| | Example 6: 229/125/1100 |
| | Example 7: 33.4/246/3350 |
| | Example 8: 300/147/276 |
| Permeability (Human Pgp transfected) MDCK $P_{app}$ (×10$^{-6}$ cm/s) A-B/B-A | Example 1: 0.5/73 |
| PPB fraction unbound Rat/dog/human | Example 1: 0.52/0.27/0.67 |
| clogP/clogD | Example 1: 3.66/1.80 |

Example 11: In Vivo Pharmacokinetics

The pharmacokinetics of compounds were studied in vivo in male Sprague Dawley rats at doses of 1 mg/kg (IV) and 10 mg/kg (PO).

Methods

Sprague Dawley rats were treated with experimental compounds via intravenous and oral administration. Three animals for each route of administration were used with serial blood sampling at ten time points post dosing of compound.

An intravenous bolus was administered at a dose of 1 mg/kg and at a concentration of 1 mgml in 40:60 dimethyl acetamide/saline (0.9% w/v saline). Animals were weighed and used if between 200-250 g. Serial blood samples were collected at 0.02, 0.08, 0.25, 0.50, 1, 2, 4, 6, 8 and 24 hours post dosing. Animals were observed for any overt clinical signs or symptoms. Blood samples were delivered into an anticoagulant (sodium heparin) and centrifuged at 4° C. Plasma samples were subsequently stored frozen at less than −20° C. prior to analysis.

Following protein precipitation with acetonitrile, samples were analysed with tandem liquid chromatography/mass spectrometry using electrospray ionisation. A full matrix curve with internal standards was employed and PK parameters were calculated.

In a similar manner, oral administration was performed by gavage at doses of 5 or 10 mg/kg at a concentration of 5 mg/ml in 1% Methyl cellulose (Sigma M7140), 0.1% Tween 80 in water. Serial samples were taken as described above.

Results

TABLE 3

| Pharmacokinetic Property | Value |
| --- | --- |
| Volume of distribution (L/kg) | Example 1: 22 |
|  | Example 5: 8.2 |
| $T_{max}$ PO (hr) | Example 1: 2.7 |
| Bioavailability (%) | Example 1: 42% |

Comparative Example 1: In Vitro Efficacy

The protocols of Example 9 were repeated for RV039 (1'-((5-(aminomethyl)-1-isopentyl-1H-benzo[d]imidazol-2-yl)methyl)spiro[cyclopropane-1,3'-indolin]-2'-one; identified in WO 2013/068769 as the compound of Example 2).

Results

TABLE 4

| RSV Fusion Assay $IC_{50}$ (nM) | RSV Plaque Reduction assay $IC_{50}$ (nM) |
| --- | --- |
| 10 | 31 |

Comparative Example 2: In Vitro Pharmacokinetics

The protocols of Example 10 were repeated for RV039, which is 1'-((5-(aminomethyl)-1-isopentyl-1H-benzo[d]imidazol-2-yl)methyl)spiro[cyclopropane-1,3'-indolin]-2'-one (identified in WO 2013/068769 as the compound of Example 2).

Results

TABLE 5

| Pharmacokinetic Property | Value |
| --- | --- |
| Liver Microsomal Stability ($T_{1/2}$; human/rat/dog) | 5/>95/>100 |
| Permeability (Human Pgp transfected) MDCK $P_{app}$ ($\times 10^{-6}$ cm/s) A-B/B-A | 0.42/49 |
| PPB fraction unbound Rat/dog/human | 0.1/0.1/0.07 |
| clogP/clogD | 3.62/1.75 |

Comparative Example 3: In Vivo Pharmacokinetics

The protocols of Example 11 were repeated for RV039 (1'-((5-(aminomethyl)-1-isopentyl-1H-benzo[d]imidazol-2-yl)methyl)spiro[cyclopropane-1,3'-indolin]-2'-one; identified in WO 2013/068769 as the compound of Example 2). RV039 was administered at doses of 1 mg/kg (IV) and 5 mg/kg (PO).

Results

TABLE 6

| Pharmacokinetic Property | Value |
| --- | --- |
| Volume of distribution (L/kg) | 47 |
| $T_{max}$ PO (hr) | 7.3 |
| Bioavailability (%) | 4.5% |

Example 11: Aqueous Formulation

The compound of Example 1 is formulated as a solution in 30% w/v captisol (i.e. sulfobutylether-beta-cyclodextrin) at pH4 according to the following procedure.

A carrier of 30% w/v captisol (i.e. sulfobutylether-beta-cyclodextrin) is prepared by weighing the required amount of captisol into a suitable vessel, adding approximately 80% of the final volume of water and magnetically stirring until a solution is formed. The carrier is then made up to volume with water.

An aqueous solution of a compound of Example 1 is prepared by weighing 175 mg of the compound into a suitable vessel and adding approximately 80% of the required volume of the carrier. Using an aqueous solution of hydrochloric acid, the pH is adjusted to pH2 and the resulting mixture is magnetically stirred until a solution is formed. The formulation is then made up to volume with carrier and the pH is adjusted to pH4 using an aqueous solution of sodium hydroxide.

Example 12: Tablet Composition

Tablets, each weighing 0.15 g and containing 25 mg of a compound of the invention are manufactured as follows:

Composition for 10,000 Tablets
Compound of the invention (250 g)
Lactose (800 g)
Corn starch (415 g)
Talc powder (30 g)
Magnesium stearate (5 g)

The compound of the invention, lactose and half of the corn starch are mixed. The mixture is then forced through a sieve 0.5 mm mesh size. Corn starch (10 g) is suspended in warm water (90 mL). The resulting paste is used to granulate the powder. The granulate is dried and broken up into small fragments on a sieve of 1.4 mm mesh size. The remaining quantity of starch, talc and magnesium is added, carefully mixed and processed into tablets.

Example 13: Injectable Formulation

| | |
|---|---|
| Compound of the invention | 200 mg |
| Hydrochloric Acid Solution 0.1M or Sodium Hydroxide Solution 0.1M q.s. to pH | 4.0 to 7.0 |
| Sterile water q.s. to | 10 mL |

The compound of the invention is dissolved in most of the water (35° C.-40° C.) and the pH adjusted to between 4.0 and 7.0 with the hydrochloric acid or the sodium hydroxide as appropriate. The batch is then made up to volume with water and filtered through a sterile micropore filter into a sterile 10 mL amber glass vial (type 1) and sealed with sterile closures and overseals.

Example 14 Intramuscular Injection

| | |
|---|---|
| Compound of the invention | 200 mg |
| Benzyl Alcohol | 0.10 g |
| Glycofurol 75 | 1.45 g |
| Water for injection q.s to | 3.00 ml |

The compound of the invention is dissolved in the glycofurol. The benzyl alcohol is then added and dissolved, and water added to 3 mL. The mixture is then filtered through a sterile micropore filter and sealed in sterile 3 mL glass vials (type 1).

Example 15 Syrup Formulation

| | |
|---|---|
| Compound of invention | 250 mg |
| Sorbitol Solution | 1.50 g |
| Glycerol | 2.00 g |
| Sodium benzoate | 0.005 g |
| Flavour | 0.0125 mL |
| Purified Water q.s. to | 5.00 mL |

The compound of the invention is dissolved in a mixture of the glycerol and most of the purified water. An aqueous solution of the sodium benzoate is then added to the solution, followed by addition of the sorbital solution and finally the flavour. The volume is made up with purified water and mixed well.

The invention claimed is:
1. A compound which is
1'-{[5-(aminomethyl)-1-(4,4,4-trifluorobutyl)-1H-1,3-benzodiazol-2-yl]methyl}-6'-fluoro-1',2'-dihydrospiro[cyclopropane-1,3'-indole]-2'-one;
or a pharmaceutically acceptable salt thereof.

2. A pharmaceutical composition which comprises the compound or a pharmaceutically acceptable salt thereof as defined in claim 1 and a pharmaceutically acceptable carrier or diluent.

3. A method of treating a subject suffering from or susceptible to an RSV infection, which method comprises administering to said subject an effective amount of the compound or a pharmaceutically acceptable salt thereof as defined in 1.

4. The method of claim 3, which includes administering one or more therapeutic agents, which is or are administered simultaneously, separately, or sequentially with the administration of the compound or a pharmaceutically acceptable salt thereof.

5. A method according to claim 4, wherein the one or more therapeutic agents is or are selected from the group consisting of:
   (i) a RSV nucleocapsid (N)-protein inhibitor;
   (ii) a protein inhibitor;
   (iii) an anti-RSV monoclonal antibody;
   (iv) an immunomodulating toll-like receptor compound;
   (v) a respiratory virus anti-viral; and
   (vi) an anti-inflammatory compound.

6. A pharmaceutical composition which comprises (a) the compound or a pharmaceutically acceptable salt thereof as defined in claim 1, and (b) one or more therapeutic agents, together with a pharmaceutically acceptable carrier or diluent.

7. A compound which is 1'-((5-(aminomethyl)-1-(tetrahydro-2H-pyran-4-yl)-1H-benzo[d]imidazol-2-yl)methyl)-6'-fluorospiro[cyclopropane-1,3'-indolin]-2'-one or a pharmaceutically acceptable salt thereof.

8. A pharmaceutical composition which comprises the compound or a pharmaceutically acceptable salt thereof as defined in claim 7 and a pharmaceutically acceptable carrier or diluent.

9. A method of treating a subject suffering from or susceptible to an RSV infection, which method comprises administering to said subject an effective amount of the compound or a pharmaceutically acceptable salt thereof as defined in claim 7.

10. The method of claim 9, which includes administering one or more therapeutic agents, which is or are administered simultaneously, separately, or sequentially with the administration of the compound or a pharmaceutically acceptable salt thereof.

11. The method according to claim 10, wherein the one or more therapeutic agents is or are selected from the group consisting of:
   (i) a RSV nucleocapsid (N)-protein inhibitor;
   (ii) a protein inhibitor;
   (iii) an anti-RSV monoclonal antibody;
   (iv) an immunomodulating toll-like receptor compound;
   (v) a respiratory virus anti-viral; and
   (vi) an anti-inflammatory compound.

12. A pharmaceutical composition which comprises (a) the compound a or a pharmaceutically acceptable salt thereof as defined in claim 7, and (b) one or more therapeutic agents, together with a pharmaceutically acceptable carrier or diluent.

* * * * *